(12) United States Patent
Kumar et al.

(10) Patent No.: US 7,098,377 B2
(45) Date of Patent: Aug. 29, 2006

(54) IEX-1 KNOCKOUT ANIMALS

(75) Inventors: Rajiv Kumar, Rochester, MN (US); Jan Van Deursen, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 10/824,632

(22) Filed: Apr. 14, 2004

(65) Prior Publication Data

US 2005/0235373 A1 Oct. 20, 2005

(51) Int. Cl.
*A01K 67/00* (2006.01)
*A01K 67/033* (2006.01)
*A01K 67/027* (2006.01)

(52) U.S. Cl. .............................. 800/18; 800/13; 800/9

(58) Field of Classification Search ................... 800/8, 800/9, 18
See application file for complete search history.

(56) References Cited

U.S. PATENT DOCUMENTS 5,973,117 A 10/1999 Onda et al.
6,399,316 B1 6/2002 Onda et al.

OTHER PUBLICATIONS

Murray, et al. (1999, Transgenic Animals in Agriculture, CAB International: Oxon, pp. 58-61).*
Mullins and Mullins (1996, J. Clin. Invest., 97: 1557-1560).*
De Keulenaer et al. (2002, Circ. Res. 90:690-696).*
Capecchi (1989, Trends in Genetics, 5: 70-76).*
Mench (1999, Transgenic Animals in Agriculture, CAB International: Oxon, pp. 251-268).*
Barbee et al., "Hemodynamics in Transgenic Mice With Overexpression of Atrial Natriuretic Factor," *Circ. Res.*, 1994, 74:747-751.
Chan and Fiscus, "Guanylyl cyclase inhibitors NS2028 and ODQ and protein kinase G (PKG) inhibitor KT5823 trigger apoptotic DNA fragmentation in immortalized uterine epithelial cells: anti-apoptotic effects of basal cGMP/PKG," *Mol. Hum. Reprod.*, 2003, 9(12):775-783.
Chan and Fiscus, "Vasorelaxant response to isoprenaline, nitric oxide donor, calcitonin gene-related peptide and vasoactive intestinal peptide in aortic rings of adult C57BL/6J mice," *Eur. J. Pharmacol.*, 2001, 431:229-236.
Chan and Fiscus, "Vasorelaxations Induced by Calcitonin Gene-releated Peptide, Vasiactive Intestinal Peptide, and Acetylcholine in Aortic Rings of Endothelial and Inducible Nitric Oxide Synthase-Knockout Mice," *J. Cardiovasc. Pharmacol.*, 2003, 41:434-443.

Charles et al., "Genomic structure, cDNA sequence, and expression of *gly96*, a growth factor-inducible immediate-early gene encoding a short-lived glycosylated protein," *Oncogene*, 1993, 8:797-801.
d'Uscio et al., "Mechanism of Endothelial Dysfunction in Apolipoprotein E-Deficient Mice," *Arterioscler. Thromb. Vasc. Biol.*, 2001, 21:1017-1022.
Feldman et al., "Validation of a mouse conductance system to determine LV volume: comparison to echocardiography and crystals," *Am. J. Physiol. Heart Circ. Physiol.*, 2000, 279:H1698-H1707.
Feldmann et al., "Expression of an immediate early gene, IEX-1, in human tissues," *Histochem. Cell Biol.*, 2001, 115:489-497.
Fiscus et al., "CGRP Release and Synergistic Interactions with Nitric Oxide: Implications for Pathogenesis of Septic Shock and the Vascular Problems of Diabetes Mellitus and Aging," *TheScientificWorld*, 2001, 1(S1):2, Abstract.
Grynkiewicz et al., "A New Generation of $Ca^{2+}$ Indicators with Greatly Improved Fluorescence Properties," *J. Biol. Chem.*, 1985, 260(6):3440-3450.
Hart et al., "Effects of avertin versus xylazine-ketamine anesthesia on cardiac function in normal mice," *Am. J. Physiol. Heart Circ. Physiol.*, 2001, 281:H1938-H1945.
Hosogai et al., "Phosphodiesterase type 5 inhibition ameliorates nephrotoxicity induced by cyclosporin A in spontaneous hypertensive rats," *Eur. J. Pharmacol.*, 2003, 477:171-178.
Im et al., "Characterization of a novel hexameric repeat DNA sequence in the promoter of the immediate early gene, IEX-1, that mediates $1\alpha25$-dihydroxyvitamin $D_3$-associated IEX-1 gene repression," *Oncogene*, 2002, 21:3706-3714.
Im et al., "Divergent Regulation of the Growth-promoting Gene *IEX-1* by the p53 Tumor Suppressor and Sp1," *J. Biol. Chem.*, 2002, 277(17):14612-14621.
Knowles et al., "Pressure-independent enahncement of cardiac hypertrophy in natriuretic peptide receptor A-deficient mice," *J. Clin. Invest.*, 2001, 107:975-984.
Kondratyev et al., "Identification and characterization of a radiation-inducible glycosylated human early-response gene," *Cancer Res.*, 1996, 56(7):1498-1502.
Krege et al., "A Noninvasive Computerized Tail-Cuff System for Measuring Blood Pressure in Mice," *Hypertension*, 1995, 25:1111-1115.
Kumar et al., "A Novel Immediate Early Response Gene, IEX-1, Is Induced by Ultraviolet Radiation in Human Keratinocytes," *Biochem. Biophys. Res. Commun.*, 1998, 253:336-341.

(Continued)

Primary Examiner—Anne M. Wehbe'
Assistant Examiner—Joanne Hama
(74) Attorney, Agent, or Firm—Fish & Richardson P.C.

(57) ABSTRACT

The invention provides methods and materials related to animals having a disrupted IEX-1 sequence. For example, the invention provides homozygous knockout (IEX-1$^{-/-}$) animals and heterozygous (IEX-1$^{-/+}$) animals.

6 Claims, 10 Drawing Sheets

OTHER PUBLICATIONS

Laemmli, "Cleavage of Structural Proteins during the Assembly of the Head of Bacteriophage T4," *Nature*, 1970,227:680-685.

Lehoux and Tedgui, "All Strain, No Gain: Stretch Keeps Proliferation at Bay via the NF-κB Response Gene *iex-1*," *Circ. Res.*, 2003, 93:1139-1141.

Li et al., "Targeted Mutation of the DNA Methyltransferase Gene Results in Embryonic Lethality," *Cell*, 1992, 69:915-926.

Lutz et al., "Calbindin $D_{28K}$ interacts with Ran-binding protein M: identification of interacting domains by NMR spectroscopy," *Biochem. Biophys. Res. Commun.*, 2003, 303:1186-1192.

Matsubara et al., "Logistic Time Constant of Isovolumic Relaxation Pressure-Time Curve in the Canine Left Ventricle. Better Alternative to Exponential Time Constant," *Circulation*, 1995, 92:2318-2326.

Ohki et al., "Identification of mechanically induced genes in human monocytic cells by DNA microarrays," *J. Hypertens.*, 2002, 20:685-691.

Ortiz et al., "Role of Endothelin and Isoprostanes in Slow Pressor Responses to Angiotensin II," *Hypertension*, 2001, 37:505-510.

Pietzsch et al., "Genomic Organization, Promoter Cloning, and Chromosomal Localization of the Dif-2 Gene," *Biochem. Biophys. Res. Commun.*, 1998, 245:651-657.

Ray et al., "Isolation of vascular smooth muscle cells from a single murine aorta," *Methods Cell Sci.*, 2002, 23:185-188.

Sanger et al., "DNA Sequencing with Chain-terminating Inhibitors," *Proc. Natl. Acad. Sci. USA*, 1977, 74(12):5463-5467.

Schäfer et al., "Human PACAP Response Gene 1 (p22/PRG1): Proliferation-Associated Expression in Pancreatic Carcinoma Cells," *Pancreas*, 1999, 18(4):378-384.

Schafer et al., "PRG1: a novel early-response gene transcriptionally induced by pituitary adenylate cyclase activating polypeptide in a pancreatic carcinoma cell line," *Cancer Res.*, 1996, 56(11):2641-2648.

Schulze et al., "Biomechanically Induced Gene *iex-1* Inhibits Vascular Smooth Muscle Cell Proliferation and Neointima Formation," *Circ. Res.*, 2003, 93:1210-1217.

Senthil et al., "Evidence of oxidative stress in the circulation of ovarian cancer patients," *Clin. Chim. Acta*, 2004, 339:27-32.

Taylor et al., "Altered Expression of Small-Conductance $Ca^{2+}$-Activated $K^+$ (SK3) Channels Modulates Arterial Tone and Blood Pressure," *Circ. Res.*, 2003, 93:124-131.

Thomas and Capecchi, "Site-Directed Mutagenesis by Gene Targeting in Mouse Embryo-Derived Stem Cells," *Cell*, 1987, 51:503-512.

Thompson and Appleman, "Multiple Cyclic Nucleotide Phosphodiesterase Activities from Rat Brain," *Biochemistry*, 1971, 10(2):311-316.

Towbin et al., "Electrophoretic transfer of proteins from polyacrylamide gels to nitrocellulose sheets: Procedure and some applications," *Proc. Natl. Acad. Sci. USA*, 1979, 76(9):4350-4354.

Tsuneyoshi et al., "$Ca^{2+}$- and Myosin Phosphorylation-independent Relaxation by Halothane in $K^+$-depolarized Rat Mesenteric Arteries," *Anesthesiology*, 2003, 99:656-665.

van Deursen, "Gene Targeting in Mouse Embryonic Stem Cells," *Meth. Mol. Biol.—Transgenic Mouse Methods and Protocols*, 1994, 209:145-158.

Weinmann and Farnham, "Identification of unknown target genes of human transcription factors using chromatin immunoprecipitation," *Methods*, 2002, 26:37-47.

Weiss et al., "Hemodynamic Determinants of the Time-Course of Fall in Canine Left Ventricular Pressure," *J. Clin. Invest.*, 1976, 58:751-760.

Wu et al., "*IEX-1L*, an Apoptosis Inhibitor Involved in NF-κB-Mediated Cell Survival," *Science*, 1998, 281:998-1001.

Yamamoto et al., "Left Ventricular Diastolic Dysfunction in Patients with Hypertension and Preserved Systolic Function," *Mayo Clin. Proc.*, 2000, 75:148-155.

Yang et al., "Validation of Conductance Catheter System for Quantification of Murine Pressure-Volume Loops," *J. Invest. Surg.*, 2001, 14:341-355.

Zhang et al., "Impaired apoptosis, extended duration of immune responses, and a lupus-like autoimmune disease in IEX-1-transgenic mice," *Proc. Natl. Acad. Sci. USA*, 2002, 99(2):878-883.

\* cited by examiner

Identification of Targeted ES Clones by Southern Blot Analysis

A. PCR Analysis of Homozygous IEX-1 Knockout Mice 926 bp→ ←1159 bp

B. RT PCR of IEX-1 Expression in various tissues of an IEX-1 Knockout and Normal Mouse 1=Intestine
2=Heart
3=Muscle
4=Skin
5=Pancreas
6=Liver
7=Thymus
8=Colon ←240bp

A.

B.

IEX-1 KNOCKOUT ANIMALS

BACKGROUND

1. Technical Field

The invention relates to IEX-1 knockout animals and methods and materials related to IEX-1 knockout animals, hypertension, and vascular smooth muscle cells.

2. Background Information

IEX-1 (also known as hdif and PPRG in humans) is an immediate early gene in humans and is known as gly96 in the mouse (Kumar et al., 1998. A novel immediate early response gene, IEX-1, is induced by ultraviolet radiation in human keratinocytes. Biochem Biophys Res Commun 253: 336–341; Kondratyev et al., 1996. Identification and characterization of a radiation-inducible glycosylated human early-response gene. Cancer Res 56:1498–1502; Schafer et al., 1999. Human PACAP response gene 1 (p22/PRG1): proliferation-associated expression in pancreatic carcinoma cells. Pancreas 18:378–384; Schafer et al., 1996. PRG1: a novel early-response gene transcriptionally induced by pituitary adenylate cyclase activating polypeptide in a pancreatic carcinoma cell line. Cancer Res 56:2641–2648; Pietzsch et al., 1998. Genomic organization, promoter cloning, and chromosomal localization of the Dif-2 gene. Biochem Biophys Res Commun 245:651–657; Charles et al., 1993. Genomic structure, cDNA sequence, and expression of gly96, a growth factor-inducible immediate-early gene encoding a short-lived glycosylated protein. Oncogene 8:797–801). The IEX-1 polypeptide was identified in endothelial and vascular smooth muscle cells (VSMCs; Kumar et al., 1998. A novel immediate early response gene, IEX-1, is induced by ultraviolet radiation in human keratinocytes. Biochem Biophys Res Commun 253:336–341; Feldmann et al., 2001. Expression of an immediate early gene, IEX-1, in human tissues. Histochem Cell Biol 115:489–497). IEX-1 is highly expressed in the endothelium and VSMCs of both arteries and veins. Recent information shows that IEX-1 is induced by biomechanical strain in cardiomyocytes, VSMCs, and monocytes, and that it inhibits cardiomyocyte hypertrophy and VSMC and the response to vascular injury (Lehoux and Tedgui, 2003. All strain, no gain: stretch keeps proliferation at bay via the NF-kappaB response gene iex-1. Circ Res 93:1139–1141; Schulze et al., 2003. Biomechanically induced gene iex-1 inhibits vascular smooth muscle cell proliferation and neointima formation. Circ Res 93:1210–1217; Ohki et al., 2002. Identification of mechanically induced genes in human monocytic cells by DNA microarrays. J Hypertens 20:685–691; and De Keulenaer et al., 2002. Identification of IEX-1 as a biomechanically controlled nuclear factor-(kappa)B target gene that inhibits cardiomyoctye hypertrophy. Circulation Research 90:685–691).

IEX-1 polypeptides are cytoplasmic and nuclear glycosylated proteins. The IEX-1 gene encodes a 156 amino acid protein with a calculated MW=16927.48 Da and an estimated pI=8.83. The protein has various sites at which post-translational modifications such as phosphorylation can potentially occur that may be mediated by cAMP-dependent kinase, protein kinase C, and various phosphatases. In addition, a glycosylation site is observed at amino acid residues 133–135. A nuclear localization signal, RKRSRR, and a co-activator motif, LXXL, are also present. On gels, the in vitro translated protein has a Mr of ~17–20,000 Da and upon glycosylation with pancreatic microsomal membranes the protein has a Mr of 27,000 Da. Western blot analysis of tissue IEX-1 shows a protein with a Mr of 27,000 on SDS-PAGE, suggesting that the protein is post-translationally modified in cells in vivo.

SUMMARY

The invention involves methods and materials related to animals having a disrupted IEX-1 sequence. For example, the invention provides homozygous knockout (IEX-1$^{-/-}$) animals and heterozygous (IEX-1$^{-/+}$) animals. Such animals can have mean arterial blood pressure measurements that are higher (e.g., about 5, 10, 15, 20, 25, 30, or more mm of Hg higher) than that of control animals (e.g., wild type littermate controls). In some embodiments, animals having a disrupted IEX-1 sequence can express reduced levels of an IEX-1 polypeptide. For example, homozygous knockout (IEX-1$^{-/-}$) animals or heterozygous (IEX-1$^{-/+}$) animals can express 10, 20, 30, 40, 50, 60, 70, 80, 90 percent less of an IEX-1 polypeptide when compared to the level of IEX-1 polypeptide expression of a wild-type control animal (IEX-1$^{+/+}$). In some cases, homozygous knockout (IEX-1$^{-/-}$) animals can lack expression of IEX-1 polypeptides. In other embodiments, animals having a disrupted IEX-1 sequence can express normal levels of an IEX-1 polypeptide.

Homozygous knockout (IEX-1$^{-/-}$) animals can be used to assess compounds for the ability to reduce high blood pressure. In addition, homozygous knockout (IEX-1$^{-/-}$) animals and heterozygous (IEX-1$^{-/+}$) animals can be used to obtain a colony of animals that are homozygous knockout (IEX-1$^{-/-}$), heterozygous (IEX-1$^{-/+}$), or wild-type (IEX-1$^{+/+}$). Such colonies can be genetically identical with the exception of the disrupted IEX-1 sequence. In addition, the homozygous knockout (IEX-1$^{-/-}$), heterozygous (IEX-1$^{-/+}$), and wild-type (IEX-1$^{+/+}$) animals of such colonies can be used to assess compounds for the ability to reduce high blood pressure that results from a disrupted IEX-1 sequence in a well controlled manner. For example, a compound's ability to reduce high blood pressure that results from a disrupted IEX-1 sequence can be assessed by comparing the results obtaining in homozygous knockout (IEX-1$^{-/-}$) animals with those obtained in heterozygous (IEX-1$^{-/+}$) animals or wild-type (IEX-1$^{+/+}$) animals.

The invention also provides methods for identifying agents that can reduce high blood pressure. For example, a test agent can be administered to a homozygous knockout (IEX-1$^{-/-}$) animal, and that animal can be monitored to determine whether the test agent reduced the animal's high blood pressure.

In general, the invention features a non-human mammal whose somatic and germ cells contain a disrupted IEX-1 sequence. The disruption resulting in the mammal having a level of blood pressure that is higher than the level observed in a control mammal lacking the disruption. The mammal can be homozygous for the disruption. The mammal can be a mouse. The mammal can have a level of blood pressure that is 5 mm of Hg higher than the level observed in a control mammal lacking the disruption. The mammal can have a level of blood pressure that is 10 mm of Hg higher than the level observed in a control mammal lacking the disruption. The mammal can have a level of blood pressure that is 20 mm of Hg higher than the level observed in a control mammal lacking the disruption. The mammal can have a level of blood pressure that is 30 mm of Hg higher than the level observed in a control mammal lacking the disruption.

In another embodiment, the invention features a non-human mammal heterozygous for a disrupted IEX-1 sequence, wherein a mammal homozygous for the disrupted IEX-1 sequence has a level of blood pressure that is higher than the level observed in a control mammal not homozygous for the disrupted IEX-1 sequence.

In another aspect, the invention features a cell, wherein the cell is obtained from a non-human mammal whose somatic and germ cells contain a disrupted IEX-1 sequence. The disruption resulting in the mammal having a level of blood pressure that is higher than the level observed in a control mammal lacking the disruption. The mammal can be homozygous for the disruption. The cell can be a vascular smooth muscle cell. The cell can be a heart cell. The cell can be an endothelial cell.

In another aspect, the invention features a cell, wherein the cell is obtained from a non-human mammal heterozygous for a disrupted IEX-1 sequence, wherein a mammal homozygous for the disrupted IEX-1 sequence has a level of blood pressure that is higher than the level observed in a control mammal not homozygous for the disrupted IEX-1 sequence. The cell can be a vascular smooth muscle cell. The cell can be a heart cell. The cell can be an endothelial cell.

In another embodiment, the invention features a cell line descended from a cell of a non-human mammal whose somatic and germ cells contain a disrupted IEX-1 sequence. The disruption resulting in the mammal having a level of blood pressure that is higher than the level observed in a control mammal lacking the disruption. The mammal can be homozygous for the disruption. The cell can be a vascular smooth muscle cell. The cell can be a heart cell. The cell can be an endothelial cell.

In another embodiment, the invention features a cell line descended from a cell of a non-human mammal heterozygous for a disrupted IEX-1 sequence, wherein a mammal homozygous for the disrupted IEX-1 sequence has a level of blood pressure that is higher than the level observed in a control mammal not homozygous for the disrupted IEX-1 sequence. The cell can be a vascular smooth muscle cell. The cell can be a heart cell. The cell can be an endothelial cell.

Another aspect of the invention features a nucleic acid construct containing a disrupted IEX-1 sequence, wherein the disruption contains a sequence inserted into an IEX-1 gene such that the disruption prevents or modifies the expression of an IEX-1 polypeptide.

Another aspect of the invention features a method for generating a mouse homozygous for an inactivated IEX-1 gene, the method including (a) providing a totipotent mouse cell that contains at least one inactivated IEX-1 gene; (b) inserting the cell into a mouse embryo; (c) implanting the embryo into a female mouse; (d) permitting the implanted embryo to develop into a neonatal mouse; (e) permitting the neonatal mouse to reach sexual maturity thereby forming a sexually mature mouse; (f) mating the sexually mature mouse to obtain at least two mice heterozygous for the inactivated IEX-1 gene; and (g) mating two of the at least two mice heterozygous for the inactivated IEX-1 gene to obtain the mouse homozygous for the inactivated IEX-1 gene, wherein the mouse homozygous for the inactivated IEX-1 gene has a level of blood pressure that is higher than the level observed in a control mouse lacking inactivated IEX-1 genes.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

Figure 1:
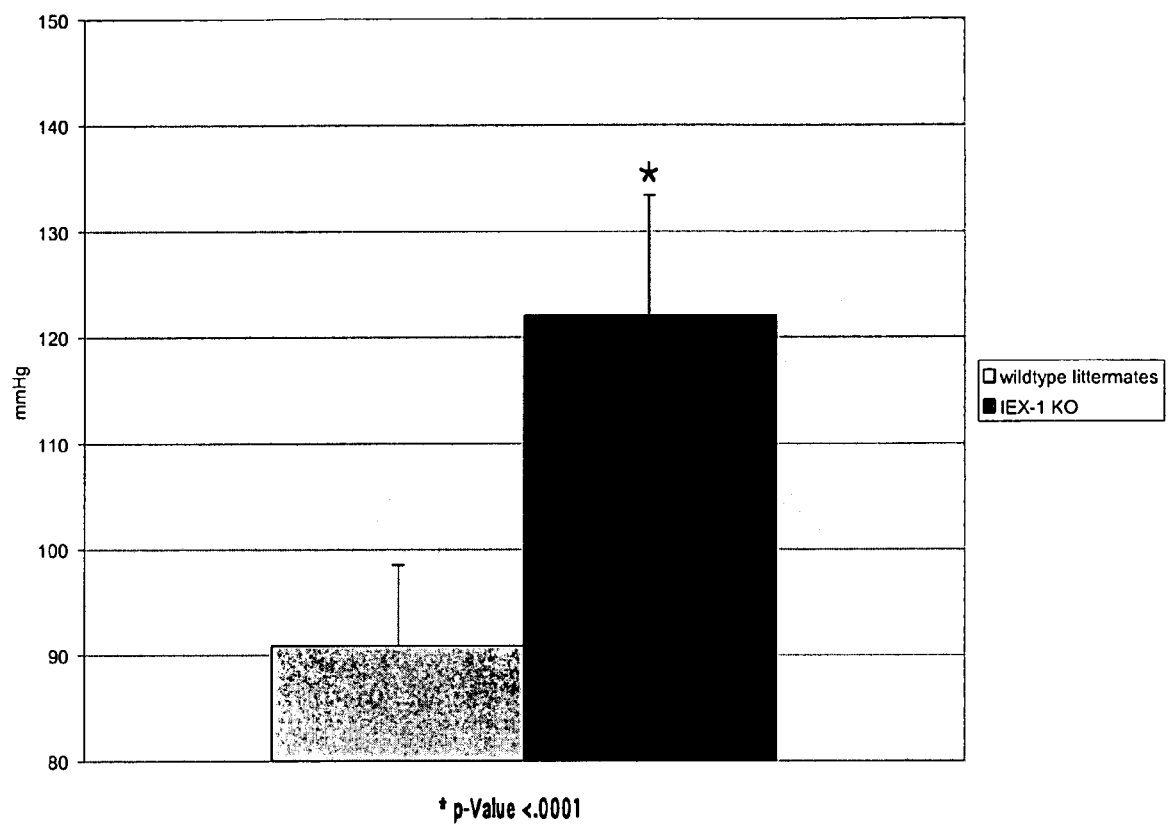
FIG. 1 is a graph plotting the BP measured with an intra-arterial catheter for IEX-1-/- mice and wild-type littermates. Similar pressures were obtained using the tail-cuff method a transducer.

The invention provides methods and materials related to non-human animals having a disrupted IEX-1 sequence. Such animals can be aquatic animals (such as fish, sharks, dolphin, and the like), farm animals (such as pigs, goats, sheep, cows, horses, rabbits, and the like), rodents (such as rats, guinea pigs, and mice), non-human primates (such as baboon, monkeys, and chimpanzees), and domestic animals (such as dogs and cats). Several techniques known in the art can be used to produce animals having a disrupted IEX-1 sequence (see, e.g., van Deursen, J. 2003. Gene targeting in mouse embryonic stem cells. 145–158 pp; and Ausbel et al., 1998. Current Protocols in Molecular Biology. New York: John Wiley & Sons, Inc.).

To create a homologously recombinant animal, a vector can be prepared which contains at least a portion of an IEX-1 gene into which a deletion, addition, or substitution has been introduced to thereby alter, e.g., functionally disrupt, the IEX-1 gene. In one embodiment, the vector is designed such that, upon homologous recombination, the endogenous gene is functionally disrupted (i.e., no longer encodes a functional protein; also referred to as a "knock out" vector). Alternatively, the vector can be designed such that, upon homologous recombination, the endogenous gene is mutated or otherwise altered but still encodes a functional IEX-1 polypeptide (e.g., the upstream regulatory region can be altered to thereby alter the expression of the endogenous IEX-1 polypeptide). In the homologous recombination vector, the altered portion of the IEX-1 gene can be flanked at its 5' and 3' ends by additional nucleic acid of the IEX-1 gene to allow for homologous recombination to occur between the exogenous gene carried by the vector and an endogenous gene in an embryonic stem cell. The additional flanking nucleic acid sequences can be of sufficient length for successful homologous recombination with the endogenous gene. Typically, several kilobases of flanking DNA (both at the 5' and 3' ends) are included in the vector (see, e.g., Thomas and Capecchi, 1987, Cell 51:503 for a description of homologous recombination vectors). The vector can be introduced into an embryonic stem cell line (e.g., by electroporation), and cells in which the introduced gene has homologously recombined with the endogenous gene can be selected (see, e.g., Li et al., 1992, Cell 69:915).

The invention also provides methods for identifying agents that can reduce high blood pressure. For example, test agents can be administered to homozygous knockout (IEX-$1^{-/-}$) animals, and the animals can be monitored to determine whether a test agent reduced an animal's high blood pressure. Any type of compound can be tested for the ability to reduce high blood pressure including, without limitation, DNA molecules (e.g., antisense oligos and DNAzymes), RNA molecules (e.g., siRNA molecules and ribozymes), small molecules, polypeptides, carbohydrates, esters, lipids, fatty acids, and aromatic compounds.

The invention will be further described in the following examples, which do not limit the scope of the invention described in the claims.

EXAMPLES

Example 1

Knockout Mammal

Figure 2:
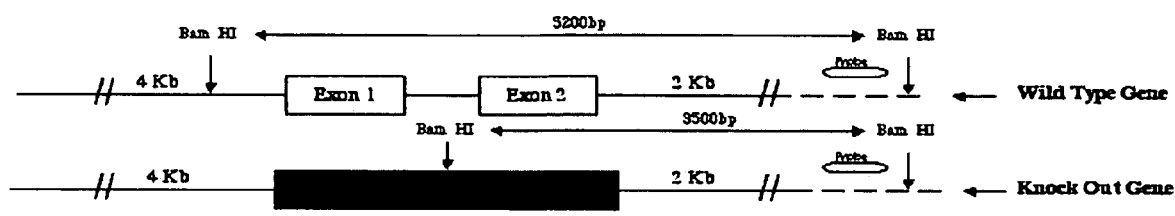
FIG. 2. Identification of a targeted ES clone in which homologous recombination has occurred in a wild type allele that has been replaced with a mutant IEX/gly96 gene comprised of a neomycin resistance gene in place of exons 1 and 2 and intron 1. 4 and 2 kbp IEX/gly96 sequences flank the Neo gene. Two such clones were isolated and used to generate IEX/gly96$^{+/-}$ mice. The probe is outside the mutant IEX-1/gly96 DNA indicating appropriate replacement of the normal allele.
Figure 2:
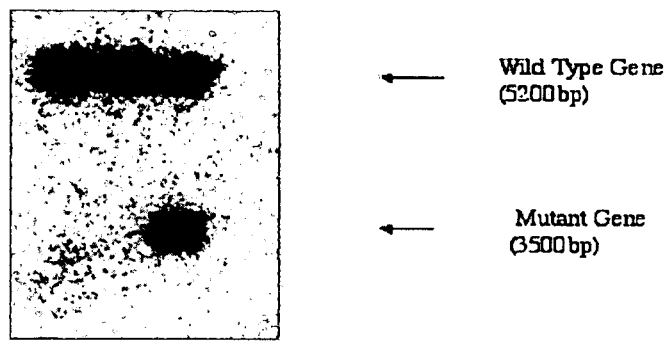

The mouse ortholog of the IEX-1 gene is known as gly96. An gly96 null mutant mouse was generated use methods similar to those described elsewhere (van Deursen, 2003, Gene targeting in mouse embryonic stem cells. 145–158 pp). For the sake of convenience, the mouse is referred to as an IEX-$1^{-/-}$ null mutant mouse as opposed to a gly96$^{-/-}$ null mouse. Briefly, a knockout mouse was generated as follows. First, the IEX-1 sequence of the mouse was obtained form the Celera mouse database. Second, genomic sequence 5' of exon 1 was amplified to generate a ~4.0 kb pair DNA sequence using 129 mouse DNA, PCR methods and primers with Hpal and Xhol sites at the 5' and 3' ends, respectively (Ausbel et al., 1998. Current Protocols in Molecular Biology. New York: John Wiley & Sons, Inc.). The product was treated with Hpal and Xhol restriction endonucleases and cloned into site A of Hpal and Xhol endonuclease-treated pNTKV knockout plasmid vector (subsequently referred to as SiteA4kb-pNTKV). Third, genomic sequence 3' of exon 2 of the IEX-1 gene was amplified using s129 mouse DNA, PCR methods and primers containing Not1 restriction endonuclease sites. The ~2.0 kb pair DNA product was treated with Not1 restriction endonuclease and cloned into Not 1 cut SiteA4kbpNTKV to yield SiteA4kbpsiteB2kbp-pNTKV, the knockout vector containing the mutant IEX-1 gene lacking exons 1 and 2, intron 1 and having a neomycin cassette in place of the 2 exons and one intron. The construct was linearized and used to electroporate embryonic stem cells. The electroporated ES cells were grown on irradiated fibroblasts and subjected to antibiotic selection with neomycin and FIAU. Two clones out of 384 ES clones were found on Southern analysis to contain the mutant construct at the appropriate site (FIG. 2). These were used inject into blastocysts which were transferred to the uterus of BCBA female mice. Chimeric black/agouti mice and subsequently heterozygous knockout (IEX-$1^{+/31}$) agouti mice were obtained by appropriate breeding methods.

Figure 3:
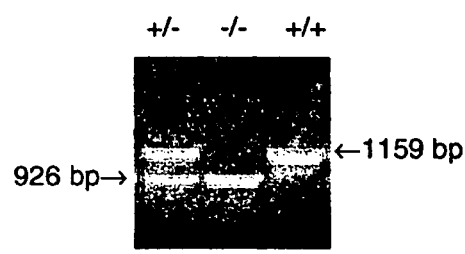
FIG. 3A. Genotyping of IEX-1/gly96 knockout (−/−), normal (+/+) and heterozygous (+/−) mice by PCR. Lane 1: DNA heterozygous mouse. Bands at 1159 and 926 bp are seen indicating the presence of a normal (1159 bp) and a mutant allele (926 bp). Lane 2: DNA homozygous knockout (−/−) mouse. One band at 926 bp is seen indicating the 2 mutant alleles. Lane 3: DNA homozygous normal (+/+) mouse. One band at 1159 bp is seen indicating the presence of two normal alleles.
FIG. 3B. RT-PCR analysis of IEX-1/gly96 mRNA in tissues of knockout and normal mice. Left, RT-PCR of RNA from tissues of a knockout (−/−) mouse. Note the absence of a band at 240 bp, the predicted size of the IEX-1/gly96 PCR product with the appropriate primers. Right, RT-PCR of RNA from tissues of a normal (+/+) mouse. Note presence of band at 240 bp, the predicted size of IEX-1/gly96 PCR product.
Figure 3:
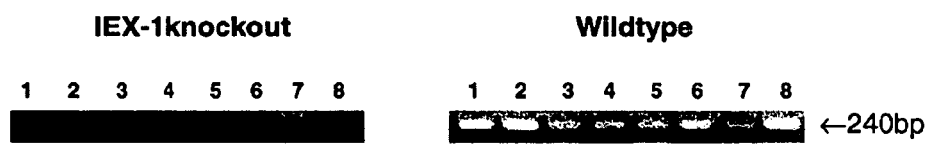

The mice were bred to form a colony of IEX-$1^{-/-}$, IEX-$1^{+/-}$, and IEX-$1^{+/+}$ mice. The mice were readily genotyped (FIG. 3). In addition, the animals were viable and exhibited the following phenotype: (1) normal viability and reproduction, (2) normal growth parameters, (3) hypertension (FIGS. 1 and 4), and (4) endothelial defects manifest as peliosis in the spleen and liver.

Figure 4:
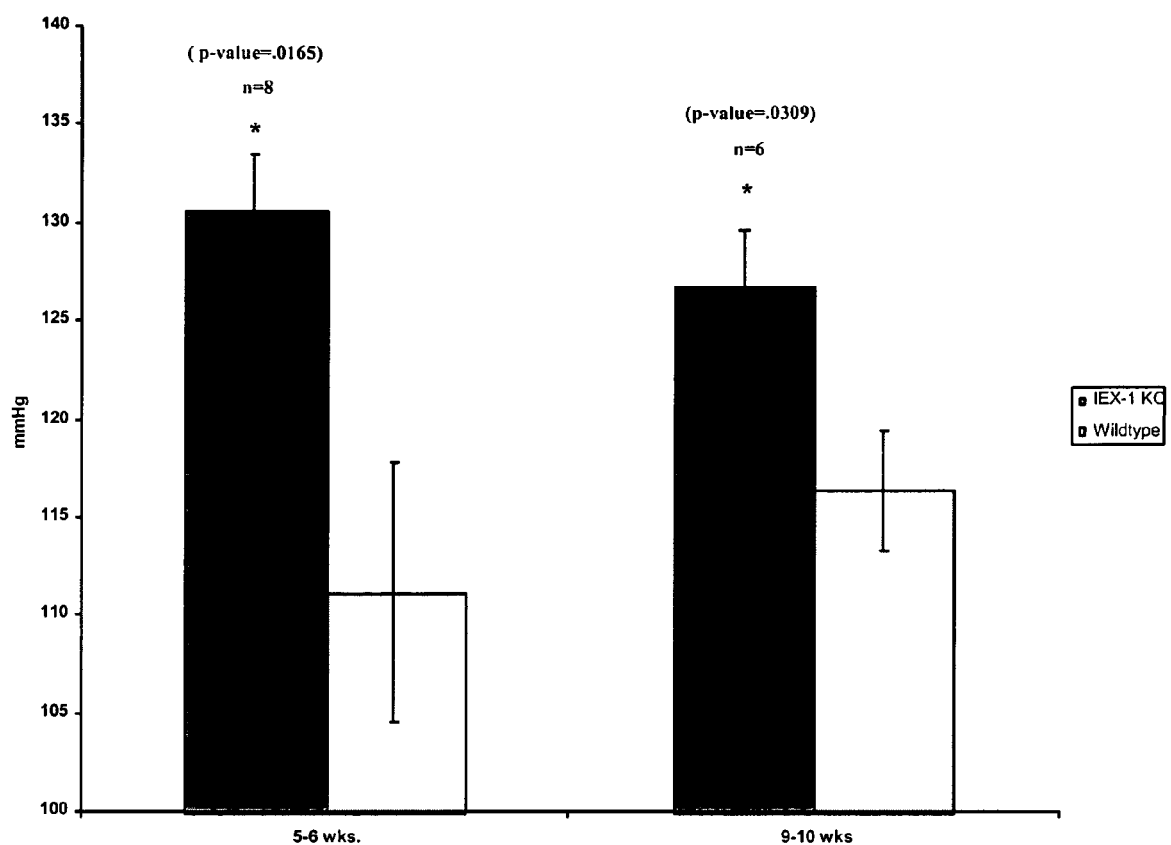
FIG. 4. IEX-1-/- or IEX-1+/+ mice had tail cuff blood pressure measurements performed on repeated occasions.

1. Blood Pressure Measurement in IEX-$1^{-/-}$ Mice:

Tail cuff blood pressures (BPs) were measured in IEX-1 knockout mice as a function of age. Conscious, awake IEX-$1^{-/-}$ mice exhibited elevated BPs measured by this method (FIG. 4). To confirm the elevation of BP in these mice, intra-aortic BPs were measured in IEX-$1^{-/-}$ mice using a high fidelity manometer-tipped catheter (Millar) placed in the antral aorta via the right carotid artery. IEX-$1^{-/-}$ mice exhibited aortic elevated systolic and diastolic BPs and elevated left ventricular pressures compared to wild-type littermates. τ, a measure of cardiac wall relaxation was elevated in the knockout mice.

2. Conductance Catheter Assessment of Left Ventricle (LV) Size and Function in the Mouse.

Figure 5:
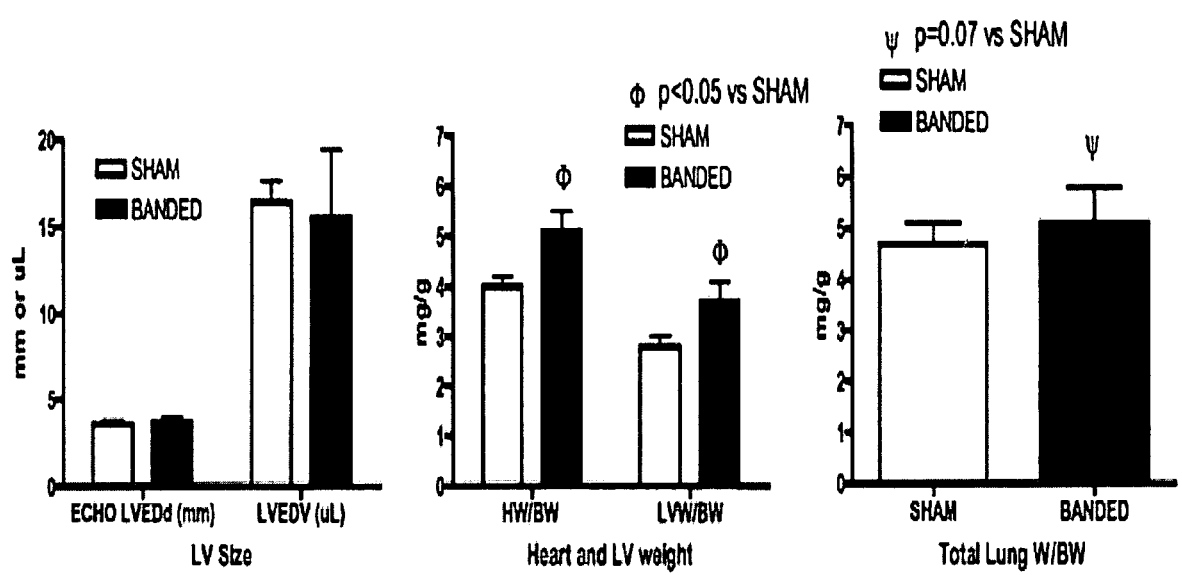
FIG. 5. LV size and mass and lung weight in banded and sham operated WT mice.
Figure 6:
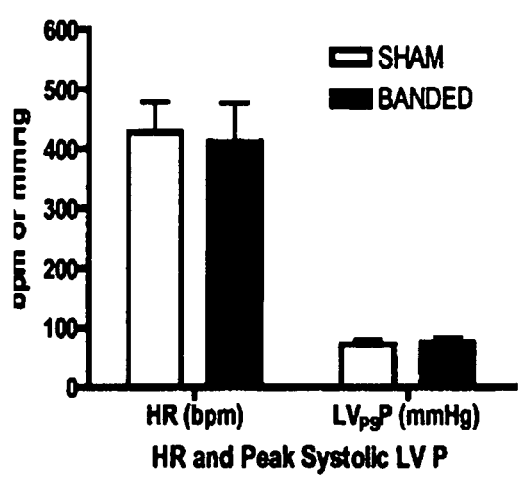
FIG. 6. Diastolic function in banded and sham operated WT mice.
Figure 6:
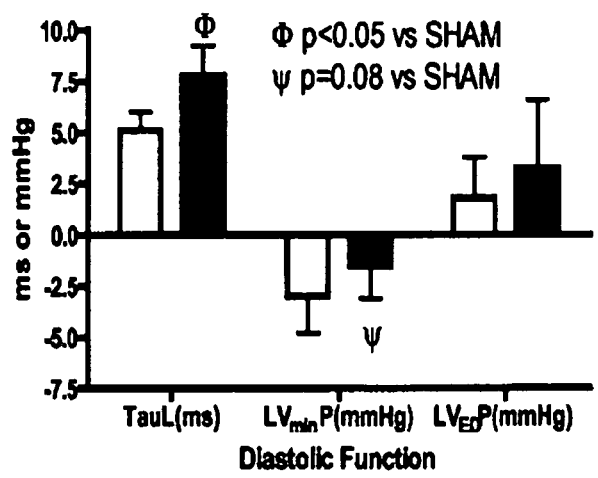
Figure 6:
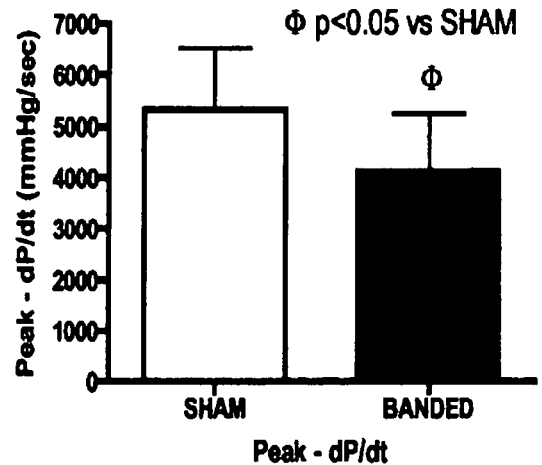
Figure 6:
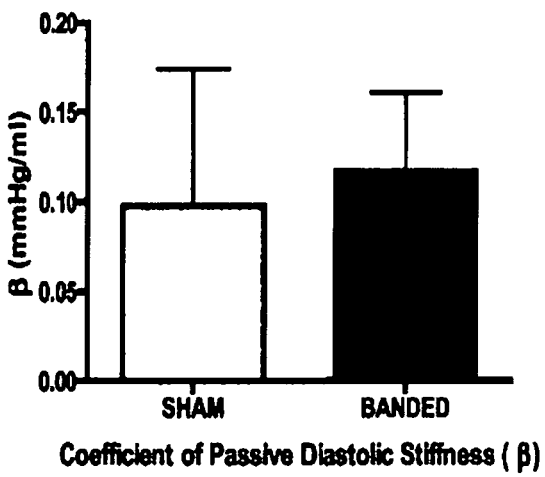
Figure 7:
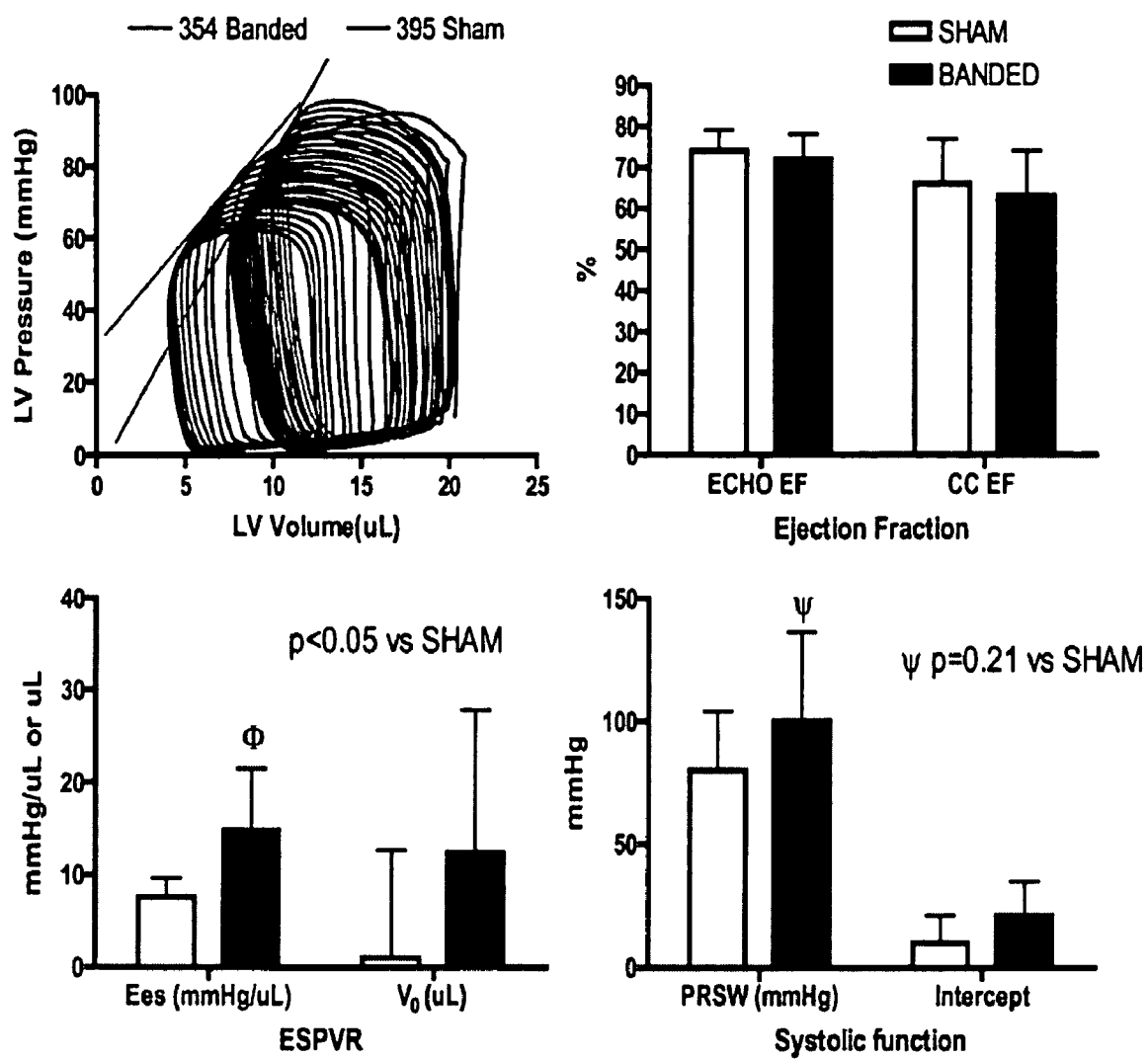
FIG. 7. Systolic function in banded and sham operated WT mice.

The effect of prolonged pressure overload (20 wks) on LV structure and function in sham operated and supra-renal aortic banded wild-type mice was assessed. LV structure and function was characterized in these mice with pressure volume analysis using a conductance catheter. The data from these studies are displayed as mean ±SD to illustrate the reproducibility of the measured parameters (FIGS. 5–7). These findings mirror those observed in dog models of hypertension where pressure volume analysis was performed with sonomicrometry and high fidelity pressure transducers. Specifically, these results indicate that LV hypertrophy is present, LV cavity size is normal, and total lung weight tends to be higher (FIG. 5). Systolic function is normal with similar ejection fraction by echo and by conductance catheter, increased systolic stiffness (Ees), and normal to enhanced preload recruitable stroke work (PRSW) (FIG. 6). Diastolic function is impaired (FIG. 7) with prolonged τ, decreased peak −dP/dt, increased $LV_{min}P$, and a trend toward higher $LV_{ED}P$. Despite hypertrophy and likely increased fibrosis (fibrosis was observed in the 3 wk model), the coefficient of passive diastolic stiffness was not significantly increased.

3. Hormonal and Electrolyte Measurements in IEX-1$^{−/−}$ Knockout Mic.

Vasoconstrictor and vasodilator substances were measured in the blood and urine of IEX-1$^{−/−}$ mice (Tables 1 and 2).

TABLE 1

24-hour Urine Excretion from Mice Fed a Normal Salt Diet

|  | IEX-1$^{−/−}$ | IEX-1$^{+/+}$ | P Value |
|---|---|---|---|
| Na mEg/24 h | 0.34 ± 0.04 | 0.28 ± .07 | NS |
| K mEg/24 h | 0.66 ± 0.07 | 0.61 ± 0.15 | NS |
| Greatinine mg/24 h | 40 ± 2 | 41 ± 4 | NS |
| Aldosterone ng/dL | 178 ± 35 | 139 ± 42.6 | NS |
| Corticosterone ng/dL | 477 ± 223 | 555 ± 101 | NS |
| Cortisol | Not detectable | Not detectable | — |
| PGE$_2$ pg/24 h | 1213 ± 277 | 984 ± 114 | NS |
| Nitrites and Nitrates μmoles/24 h | 3.5 ± 0.6* | 1.8 ± 0.4 | P < 0.05 |
| cGMP pmol/24 h | 34.8 ± 10.3 | 36.3 ± 6.9 | NS |
| Norepinephrine plus Epinephrine μg/mg creatinine | 0.053 ± 0.019 | 0.046 ± 0.026 | NS |

TABLE 2

Plasma/Serum Concentrations

|  | IEX-1$^{−/−}$ | IEX-1$^{+/+}$ | P Value |
|---|---|---|---|
| Ang II | 517 ± 218 | 275 ± 148 | NS |

The most striking difference was in urinary nitrate and nitrate concentrations that were elevated in IEX-1 knockout mice. Despite the increases in urinary nitrite and nitrate production, urinary cGMP concentrations were normal. This suggests a resistance to the vasodilator effects of nitric oxide.

4. Western Blot Analysis of Endothelial NO Synthase in Aortas of IEX-1 Knockout and Wild Type Mice.

Figure 8:
FIG. 8. Analysis of eNOS ($M_r$ 135 K) expression by Western blotting. Panel A: IEX-1$^{-/-}$ aorta; Panel B: IEX$^{+/+}$ aorta.
Figure 8:
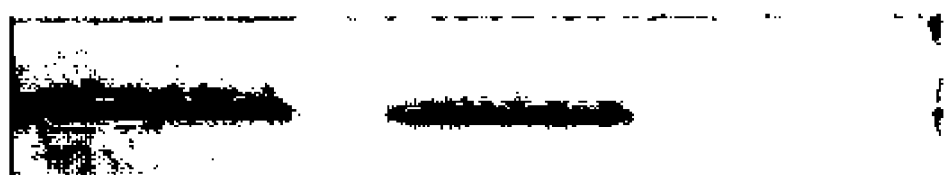

A semi-quantitative assessment of endothelial NO synthase in IEX-1 knockout and wild type mice was made. The amounts of eNOS were increased in aortas of IEX-1 knockout mice as compared with wild type mice (FIG. 8). These results demonstrate that the increase in urinary nitrite and nitrate concentrations can be contributed by increased NO production in the blood vessels of IEX-1 knockout mice.

5. Measurement of Responses to Vasodilators and Vasoconstrictors in Aortic Rings of IEX-1$^{−/−}$ Mice.

Figure 9A:
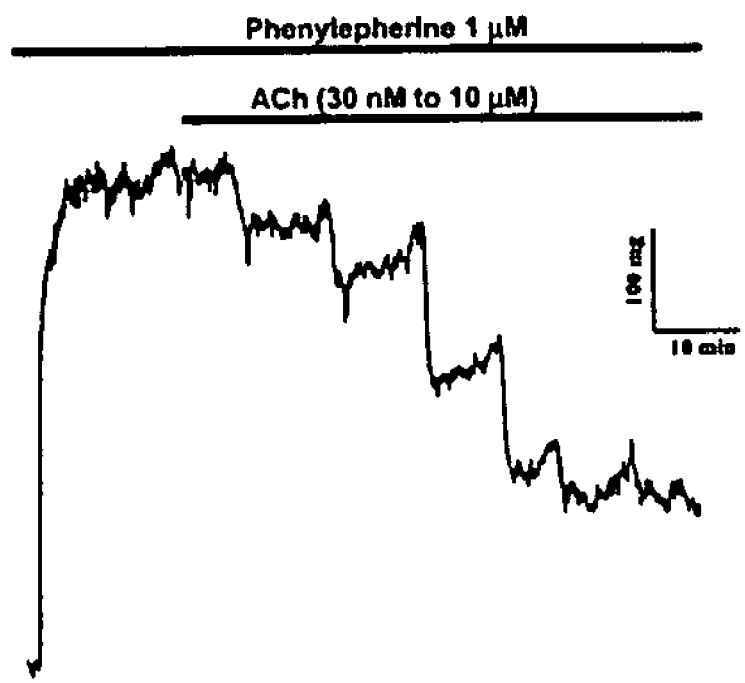
FIG. 9A. Aortic rings of wild type mice were contracted with phenylephrine and subsequently treated with acetylcholine.
Figure 9B:
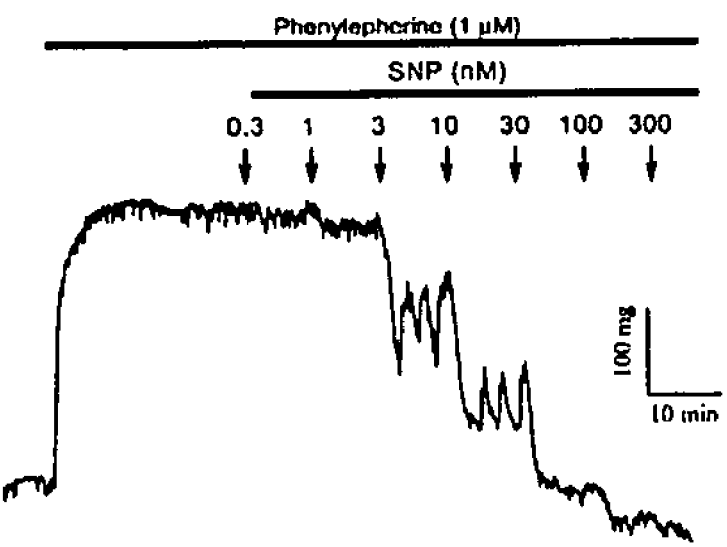
FIG. 9B. Aortic rings of wild type mice were contracted with phenylephrine and subsequently treated with sodium nitroprusside.

Contraction and vasodilation experiments were used to ascertain the presence of resistance to NO in the vessels of IEX-1$^{−/−}$ mice. FIGS. 9A and 9B show typical responses of aortic rings with intact endothelium to phenylephrine (PE) followed by treatment with acetylcholine (Ach) or sodium nitroprusside. With Ach endothelium-dependent relaxation was noted. The Ach-mediated vasorelaxation was abolished by removal of endothelium. The response to SNP was retained in the absence of endothelium.

Figure 10:
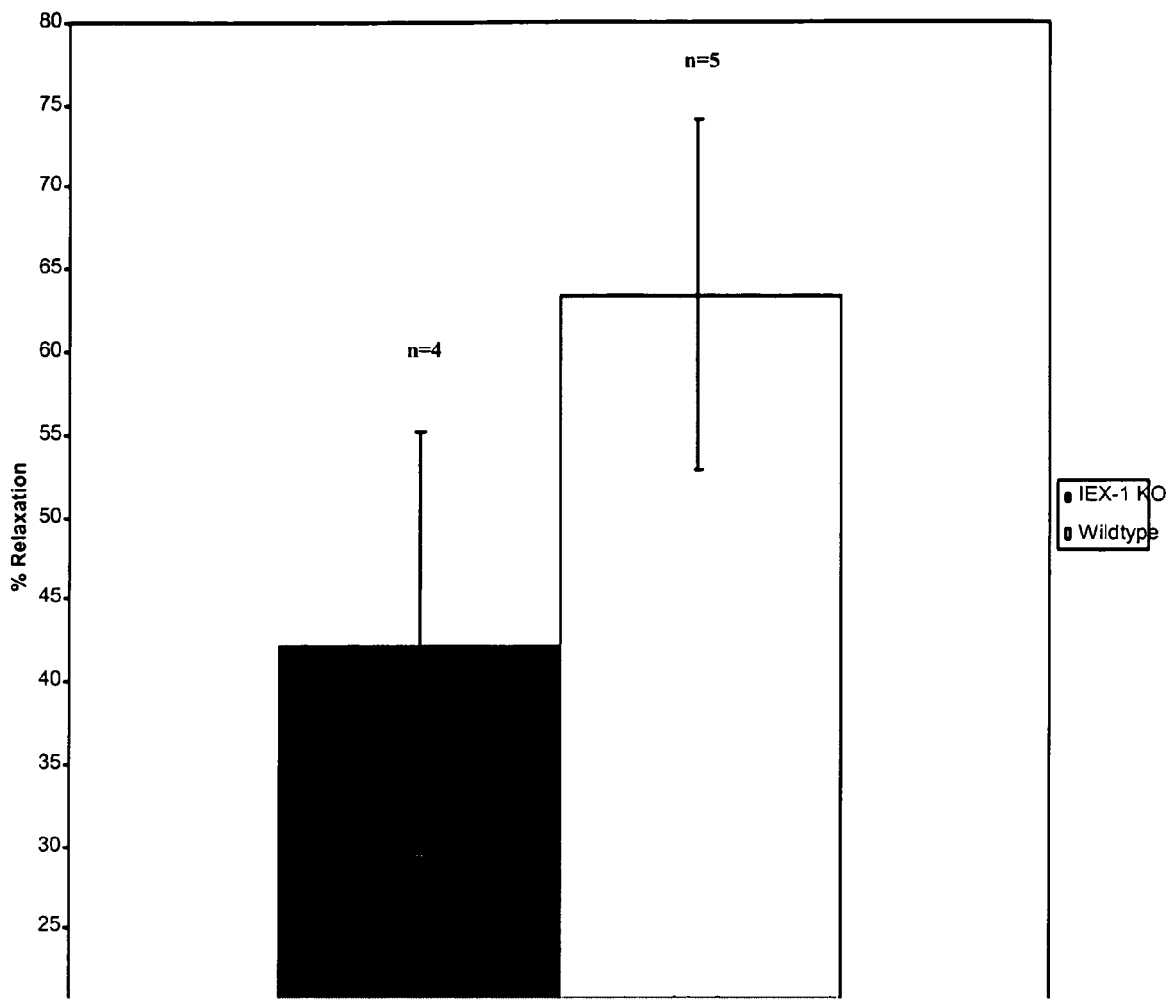
FIG. 10. Reduced Ach-mediated relaxation of contracted aortic rings (intact endothelium) in IEX-1 knockout mice in comparison with wild type mice.

Treatment of IEX-1$^{+/+}$ rings and IEX-1$^{−/−}$ with acetylcholine revealed reduced vasodilation in the IEX-1$^{−/−}$ rings (FIG. 10). This suggests a resistance to endogenously produced NO. Following sodium nitroprusside treatment, vasorelaxation was observed in both wild-type and knockout mouse aortas. Given the limited number of experiments, however, it is not possible to categorically state whether there are differences between responses in the two types of mice.

6. Yeast Two-Hybrid Experiments Using IEX-1 as Bait Protein.

Yeast Gal 4 2-hybrid experiments (Matchmaker systems, Clontech) were performed using IEX-1 as the "bait" (cloned in the pBGTK7 vector) and a kidney cDNA library in the pACT vector. Proteins expressed from the latter library in *Saccharomyces cerevisiae*, AH109 cells, were examined for their ability to be found by IEX-1 expressed from the pBGKT7 vector by nutrient auxotrophy and galactosidase activity. 50+interacting clones were obtained. Sequencing of the inserts in these clones yielded one exceptionally important result. IEX-1 binds to a calcium-modulating cyclophilin ligand (CAML), which plays an important role in cell signaling in lymphocytes and many other cells.

7. Summary

Taken together, these results demonstrate that IEX-1 null mutant mice exhibit significant hypertension, and peliosis of the spleen and liver. In addition, the mice have defects in NO signaling in the blood vessel wall. This suggests a novel mechanism for the occurrence of hypertension. The IEX-1 null mutant mice thus represents an ideal opportunity in which to study both the mechanisms of hypertension and alterations in vascular remodeling following injury.

Example 2

Influence of IEX-1 on BP

IEX-1 may influence BP by increasing systemic vascular resistance, specifically by altering the response to the nitric oxide (NO) in the wall of blood vessels. This possibility is based on the observations that IEX-1 knockout mice have: (1) elevated aortic endothelial nitric oxide synthase concentrations; (2) elevated urinary nitrite and nitrate excretion; (3) normal urinary 3' 5' cyclic guanosine monophosphate concentrations; and (4) reduced acetylcholine-induced vasorelaxation of phenylephrine contracted aortic rings.

The following experiments can be performed to determine whether hypertension in IEX-1 knockout mice is due to increases in cardiac output or increases in peripheral vascular resistance. If the hypertension is due to increases in peripheral vascular resistance and endothelial dysfunction, then the physiological and biochemical basis for this abnormality can be elucidated. Briefly, blood pressure and cardiac and vascular function can be assessed in IEX-1 knockout mice as a function of age, and compared to those parameters seen in wild type animals. In addition, hormones, and vasoconstrictor or vasodilator factors known to alter blood pressure can be evaluated in vivo in knockout mice in order to ascertain how IEX-1 alters vascular tone. If specific factors or systems known to alter vascular tone are abnormal in IEX-1 null mutant mice (e.g. the nitric oxide system), then agonists/antagonists of that system can be administered to determine whether BP responses to such agents are blunted/accentuated in vivo.

1. Biochemical and Cardiovascular Phenotype of Male IEX-1$^{−/−}$ mice, and Measurement of Hormonal Factors Known to Alter Blood Pressure.

IEX-1$^{+/-}$ mice are bred with one another to obtain homozygous knockout (IEX-1$^{-/-}$), homozygous normal (IEX-1$^{-/+}$), and heterozygous (IEX-1$^{-/+}$) littermate mice. Fifteen, male mice in each category, and for each time point, are placed on a standard salt diet (0.27% Na$^+$, 0.28% Cl$^-$, and 0.77% Ca$^{2+}$, Teklad diet 8746, Harlan-Teklad). The male mice are examined to minimize the effects of gender on the variables to be examined. The mice are examined at 3, 6, 12 and 15 months of age for the following variables.
  a) Number of surviving mice.
  b) Blood pressure by the tail cuff plethysmography (n=15).
  c) Blood pressure by telemetry in conscious mice in each category (n=15).
  d) Cardiac echocardiography (n=15).
  e) Blood, aortic and left ventricular pressures, LV volume, arterial stiffness (Ea), LV systolic and diastolic stiffness (β), LV relaxation (τ), cardiac output, and peripheral vascular resistance in mice using a conductance catheter (Millar) (n=15).
  f) Plasma or serum sodium, potassium, blood urea nitrogen, and creatinine.
  g) Plasma renin activity, direct (active) renin and angiotensin II concentrations.
  h) Plasma epinephrine, and norepinephrine concentrations.
  i) Plasma corticosterone and aldosterone concentrations.
  j) Plasma nitric oxide and thiobarbituric acid reactive substances.
  k) Plasma isoprostane concentrations.
  l) Plasma endothelin-1 concentrations.
  m) Urinary sodium, potassium, and creatinine concentrations.
  n) Urinary corticosterone, and aldosterone excretion.
  o) Urinary epinephrine, and norepinephrine excretion.
  p) Urinary prostaglandin E2 metabolites, prostaglandin 6 ketoF1α, and 2,3 dinor-thromboxane B2.
  q) Urinary nitrite and nitrate excretion.
  r) Urinary cGMP and cAMP excretion.
  s) Measurement of aortic endothelial nitric oxide synthase activity, cGMP and cAMP concentrations, guanylyl cyclase activity, adenylyl cyclase activity, cGMP kinase activity, cGMP and cAMP phosphodiesterase activity and myosin light chain kinase activity.
  t) Western blot analysis of the aorta and large blood vessels for endothelial, inducible and neuronal nitric oxide synthase, p47-phox, soluble guanylyl cyclase, cGMP kinase, type 5 phosphodiesterase (cGMP specific), myosin light chain kinase and phospho-myosin light chain kinase.
  u) Gross and histological examination of heart, lungs, aorta and large blood vessels, kidney, liver, and spleen.
  v) Atherosclerotic plaque area in aorta.

The following results are possible. The IEX-1$^{-/-}$ knockout mice can be hypertensive throughout their lives and can have premature cardiac hypertrophy, renal failure, and stroke. Arteriosclerosis and nephrosclerosis can be accelerated in the knockout mice. Peliosis and intra-organ hemorrhage can be observed and can become more marked with age. Cardiac output can be normal, and BP increases can be due to changes in systemic arterial resistance.

An increase in the concentration of nitrites and nitrates reflective of increased nitric oxide synthesis can be observed. This can be supported by the up-regulation of aortic endothelial nitric oxide synthase activity and protein, and increased NO concentrations in plasma. Cyclic GMP in the urine can be inappropriately low if there is a resistance to NO action. This can be supported by decreased aortic guanylyl cyclase activity, diminished cGMP concentrations, and a reduction in cGMP kinase and myosin light chain kinase activity and amount. If circulating NO are low, this can account for the poor stimulation of guanylate cyclase and cGMP formation in the blood vessel wall. Since eNOS amounts can be elevated, an increase in degradation of NO can be the cause of low NO levels. An increase in circulating TBARs and isoprostanes and an increase in blood vessel p47-phox can indicate increased degradation of NO, and reduced stimulation of guanylate cyclase as a cause for low cGMP levels.

2. Response of Blood Pressure in IEX-1$^{-/-}$ Mice to the Nitric Oxide Donor, Sodium Nitroprusside.

Urinary nitrite and nitrate excretion were increased in IEX-1$^{-/-}$ mice, whereas cGMP excretion was normal. Despite this, IEX-1$^{-/-}$ mice exhibited elevated BPs. This suggests that there are alterations in the responsiveness to endogenously generated NO in IEX-1$^{-/-}$ mice.

To test whether this is the case, sodium nitroprusside (SNP) is administered in increasing doses to 3–4 month-old anesthetized IEX-1$^{-/-}$ mice (n=10) or control littermate IEX-1$^{+/+}$ mice (n=10). Mice are anesthetized, and carotid artery catheters are placed for determination of mean arterial pressure. Infusions of sodium nitroprusside (SNP, 0, 5, 10, 30, 100 and 150 μg/kg per min) for 5 min are given and the half-maximal dose of SNP is determined.

The following result is possible. A reduced response to SNP in the IEX-1$^{-/-}$ mice compared to the wild-type littermate mice can be observed.

3. Response of Blood Pressure in IEX-1$^{-/-}$ Mice to Inhibition of NOS Activity.

IEX-1$^{-/-}$ mice exhibited increased eNOS concentrations in the aorta. These mice are likely to be excessively sensitive to the blockade of NO synthesis. Blood pressure is predicted to increase greatly in IEX-1$^{-/-}$ mice relative to control mice when L-NAME is administered.

To assess whether IEX-1$^{-/-}$ mice are excessively sensitive to L-NAME, 3–4 month-old IEX-1$^{-/-}$ mice (n=10) or control littermate IEX-1$^{+/+}$ mice (n=10) are placed in metabolic cages for 1 week and are fed a normal sodium diet. Blood pressure is measured daily. On days 5–7, urine is collected for the measurement of sodium, potassium, creatinine, nitrite and nitrate, and cGMP. On day 8, the mice are given L-NAME in their drinking water. Blood pressure is measured daily. On days 12–14, urine is collected for the measurement of sodium, potassium, creatinine, nitrite and nitrate, and cGMP.

The following result is possible. A much more dramatic increase in BP in the IEX-1$^{-/-}$ mice compared to the wild-type littermate mice can be observed.

4. Effect of Dietary Sodium on Blood Pressure of IEX-1$^{-/-}$ Mice.

BP can be modulated by Na$^+$ balance, and volume-dependent hypertension can be detected by decreasing dietary salt intake. To determine whether this is the case in EX-1$^{-/-}$ mice, 15 IEX-1$^{-/-}$, 15 IEX-1$^{+/-}$, and 15 IEX-1$^{+/+}$ male mice, age 3 months, are fed a normal, low, and high salt diet sequentially (10 d on each diet), and BP and relevant hormone levels are measured. IEX-1$^{+/-}$ mice are bred with one another to obtain homozygous male knockout (IEX-1$^{-/-}$), homozygous normal (IEX-1$^{+/+}$), and heterozygous (IEX-1$^{-/+}$) littermate mice. Fifteen, male, 3 month-old mice in each category are placed on: a standard salt diet (0.27% Na$^+$, Harlan-Teklad diet 8746), d 1–10; a low salt diet (0.01% Na$^+$, Harlan-Teklad diet 90228), d 11–20; and a high salt diet (3.2% Na$^+$Harlan-Teklad diet 92012), d21–30. On each day of each dietary period, BP is measured by tail-cuff plethysmography. From day 8–10 of each dietary period, the mice are placed in metabolic cages, and urine samples are collected for the measurement of the following urinary analytes: sodium, potassium, creatinine, corticosterone, aldosterone, prostaglandin E2 metabolites, prostaglandin 6 ketoF1α, and 2,3 dinor-thromboxane B2, nitrite and nitrate, cGMP and cAMP.

The following results are possible. If volume is playing an important role in the genesis of hypertension, a low salt diet can result in a more significant reduction in BP in the IEX-1$^{-/-}$ mice compared to normal littermates. The IEX-1$^{-/-}$ mice can have an exaggerated response to salt loading with marked increases in BP. On the other hand, if the model of NO resistance is correct, salt deprivation can have only a modest effect on BP.

5. Response of Blood Pressure in IEX-1 Knockout Mice to Ang II Blockade with Losartan.

The hypertension seen in IEX-1 knockout mice might be due to small increases in Ang II levels that may not be easily detected in blood. In these circumstances, the administration of an Ang II receptor antagonist may unmask subtle increases in Ang II activity. IEX-1$^{+/-}$ mice are bred with one another to obtain homozygous male knockout (IEX-1$^{-/-}$), homozygous normal (IEX-1$^{+/+}$), and heterozygous (IEX-1$^{-/+}$) littermate mice. Fifteen, male, 3 month-old mice in each category, are placed on a standard salt diet (0.27% Na$^+$, Harlan-Teklad diet 8746) for a period of 10 d before the experiment. On each day, BP is measured by tail-cuff plethysmography. From day 8–10, the mice are placed in metabolic cages, and urine samples are collected for the measurement of the following analytes: sodium, potassium, creatinine, corticosterone, aldosterone, prostaglandin E2 metabolites, prostaglandin 6 ketoF1α, and 2,3 dinor-thromboxane B2, nitrite and nitrate, cGMP and cAMP.

On day 11, they are given 30 mg/kg/day of losartan in their drinking water. These doses were verified to block Ang II activity by others (Ortiz et al., 2001, Role of endothelin and isoprostanes in slow pressor responses to angiotensin II. *Hypertension* 37:505–510). On days 12–17, BP is measured by tail-cuff-plethysmography. On days 15–17, they are placed in metabolic cages for the collection of urine and measurement of variables noted above.

The following results are possible. If the hypertension is contributed to by an increase in Ang II in IEX-1 knockout mice, then BP can fall more significantly in the knockout mice than in the normal littermates. An intermediate response can be noted in the heterozygotes.

6. Response of Blood Pressure in IEX-1 Knockout Mice to Tempol or Vitamin E.

It is possible that the hypertension seen in IEX-1 knockout mice might be due to increases oxidative stress that may not be easily detected in blood by measurement of isoprostanes and T-BARS, or by a reduction in circulating NO levels, or in the urine by measurement of 2,3 dinor-thromboxane B2. In these circumstances, the administration of tempol (a superoxide dismutase mimetic) or vitamin E (an anti-oxidant) may unmask subtle increases in superoxide anion activity. IEX-1$^{+/-}$ mice are bred with one another to obtain homozygous male knockout (IEX-1$^{-/-}$), homozygous normal (IEX-1$^{+/+}$), and heterozygous (IEX-1$^{-/+}$) littermate mice. Fifteen, male, 3 month-old mice in each category are placed on a standard salt diet (0.27% Na$^+$, Harlan-Teklad diet 8746) for a period of 10 days before the experiment. BP is measured daily by tail-cuff plethysmography. From day 8–10, the mice are placed in metabolic cages, and urine samples are collected for the measurement of the following analytes: sodium, potassium, creatinine, corticosterone, aldosterone, prostaglandin E2 metabolites, prostaglandin 6 ketoF1α, and 2,3 dinor-thromboxane B2, nitrite and nitrate, cGMP and cAMP.

On day 11, they are given 1 mmol/L of tempol in their drinking water or 5000 IU/kg of diet vitamin E for a period of 20 d. The doses of tempol or vitamin E were verified to block Ang II mediated increases in isoprostanes by others (e.g., Ortiz et al., 2001, Role of endothelin and isoprostanes in slow pressor responses to angiotensin II. *Hypertension* 37:505–510). BP is measured daily by tail-cuff-plethysmography. On days 28–30, they are placed in metabolic cages for the collection of urine and measurement of variables noted above.

The following result is possible. If the hypertension is contributed to by activation of oxidative stress in IEX-1 knockout mice, then BP can fall more significantly following tempol or vitamin E treatment in the knockout mice than in the normal littermates. If adequate reduction in the degree of oxidative stress is not observed, catalase can be administered in conjunction with tempol, or Mn-TBAP (Mn(III) tetrakis-(4-benzoic acid) porphyrin can be used, to prevent the excessive formation of hydroxyperoxide ($H_2O_2$).

7. Response of Blood Pressure in IEX-1 Knockout Mice to Endothelin Blockade.

As noted earlier, it is possible that the hypertension seen in these IEX-1 knockout mice might be due to small increases in ET levels that may not be easily detected in blood. In these circumstances, the administration of an ET receptor antagonist may unmask subtle increases in ET activity. IEX-1$^{+/-}$ mice are bred with one another to obtain homozygous male knockout (IEX-1$^{-/-}$), homozygous normal (IEX-1$^{+/+}$), and heterozygous (IEX-1$^{-/+}$) littermate mice. Fifteen, male, 3 month-old mice in each category are placed on a standard salt diet (0.27% Na$^+$, Harlan-Teklad diet 8746) for a period of 10 days before the experiment. BP is measured daily by tail-cuff plethysmography. From day 8–10, the mice are placed in metabolic cages, and urine samples are collected for the measurement of the following analytes: sodium, potassium, creatinine, corticosterone, aldosterone, prostaglandin E2 metabolites, prostaglandin 6 ketoF1α, and 2,3 dinor-thromboxane B2, nitrite and nitrate, cGMP and cAMP.

On day 11, they are given 30 mg/kg/day of bosentan (a blocker of both $ET_A$ and $ET_B$ receptors) in their drinking water. These doses were verified to block ET activity by others. On day 12–20, BP is measured by tail-cuff-plethysmography. On day 18–20, they are placed in metabolic cages for the collection of urine and measurement of variables noted above.

The following result is possible. If the hypertension is contributed to by ET-dependent mechanisms in IEX-1 knockout mice, then BP can fall more significantly in the knockout mice than in the normal littermates.

Example 3

Methods for Assessing Mice

Characterization of the Cardiovascular Phenotype of IEX-1 Knockout Mice.

Instantaneous assessment of pressure and volume using the conductance catheter is used for hemodynamic assessment of LV function and structure. This is used to allow assessment of LV relaxation and systolic and diastolic stiffness concurrently. The specific methodologies and equipment utilized are outlined herein.

Conscious systolic BP and heart rate: After a one-week training period, systolic BP is measured for five days in conscious mice using a four-mouse automated tailcuff instrument with computerized data acquisition (Visitech System, Apex, N.C.). This system was validated to correlate with intra-arterial measurements of BP (Krege et al., 1995. A noninvasive computerized tail-cuff system for measuring blood pressure in mice. Hypertension 25:1111–1115). The systolic pressure and heart rate to be measured each day of the five-day data collection period are averaged and reported.

Anesthetized studies: Murine echocardiography and LV catheterization are performed under anesthesia. Avertin (2,2, 2-Tribromoethanol, Fluka Chemika) 0.015 cc/g body weight intraperitoneal (IP) with supplemental dosing (0.1 cc) as needed was found to be superior to xylazine/ketamine with more physiologic heart rates and determined that heart rates below 300 bpm are non-physiologic in the mouse (Hart et al., 2001. Effects of avertin versus xylazine-ketamine anesthesia on cardiac function in normal mice. Am J Physiol Heart Circ Physiol 281:H1938–1945).

LV catheterization: Mice are anesthetized with avertin and an endotracheal tube is placed via a tracheostomy. The mice are mechanical ventilated (Harvard Instruments Rodent Ventilator Model 683) and are placed on a heated temperature-controlled surgical table. If the level of anesthesia does not completely abolish respiratory drive, additional anesthetic and pancuronium are given as loops for end-systolic and end-diastolic pressure volume analysis is obtained in the absence of respiratory related fluctuations in volume and pressure with the ventilator briefly suspended. The right carotid artery is exposed and a pre-calibrated four electrode conductance-pressure sensor catheter (1.4 French, Millar Instruments, Houston, Tex.) is positioned in the left ventricle. The catheter is interfaced to a pressure conductance unit (Millar Instruments, MPCU-200) and a power lab/four SP (ND Instruments, NSW Australia) AD converter and is displayed in real time using a dual display flat screen. Thus, the catheter placement can be monitored in regards to the size and shape of the pressure volume loop.

The conductance signal is converted to a left ventricular volume ($V=(1/\alpha)*(rho*L^2)*([G-G_P])$), where $\alpha$ is an adjustment constant (assumed to be 1 in mouse studies), rho is the specific resistivity of blood, L is the distance between electrodes, G is total conductance, and $G_P$ is the parallel conductance. Briefly, the catheter is calibrated ex vivo where the conductance signals corresponding to incremental increases in volume of blood of known quantities is assessed and rho determined. Once the catheter is in place, it measures the conductance of the blood in the LV chamber and the parallel conductance associated with the myocardium and surrounding tissues. To correct for the effect of the myocardium, a parallel conductance volume coefficient is determined by injecting 0.1 ml of 15% hypertonic saline (via the jugular vein) and collecting the pressure volume data during increases in volume without changes in pressure. The isochronal end systolic and end diastolic volumes are then graphed, and the point at which that relationship intersects the line of unity indicates a cavity volume of zero and this factor corrects for the conductance provided by the myocardium. This calibration procedure was performed repeatedly, and a direct relationship between the parallel conductance volume coefficients and the size of the mouse was noted. Thus, the parallel conductance volume coefficients are intermittently assessed, and in mice where it is not assessed, a weight adjusted coefficient from a database is used, which is consistent with those described in similarly sized mice in the literature (Yang et al., 2001. Validation of conductance catheter system for quantification of murine pressure-volume loops. J Invest Surg 14:341–355; and Feldman et al., 2000. Validation of a mouse conductance system to determine LV volume: comparison to echocardiography and crystals. Am J Physiol Heart Circ Physiol 279: H1698–1707).

Variably loaded beats are obtained by gentle compression of the abdominal wall producing a decrease in venous return. Representative examples of pressure volume loops are obtained in different mice at steady state, during reduction in preload (abdominal compression) to obtain variably loaded beats and during hypertonic saline infusion to increase preload as part of the calibration procedure. Parameters that are obtained or derived from the pressure measurements alone include LV systolic, minimum and end-diastolic pressure, maximal rates of pressure change (max and min dP/dt), and the time constant of isovolumic relaxation (tau). Tau is calculated using the method of Weiss ($Tau_W$; zero asymptote) and by the logistic method ($Tau_L$; floating asymptote) (Matsubara et al., 1995. Logistic time constant of isovolumic relaxation pressure-time curve in the canine left ventricle. Better alternative to exponential time constant. Circulation 92:2318–2326; and Weiss et al., 1976. Hemodynamic determinants of the time-course of fall in canine left ventricular pressure. J Clin Invest 58:751–760). Data derived from pressure volume analysis can include LV end-systolic and end-diastolic volume, cardiac output, LV pressures (minimum, end-diastolic and end-systolic), ejection fraction and during preload alteration the end-systolic pressure volume relationship (Ees, the slope of the end-systolic PV relationship), the end diastolic pressure volume relationship where a stiffness constant ($\beta$) is calculated from the linear ($P_{ed}=\beta V_{ed}+V_o$) or exponential relationship of end-diastolic pressure and volume ($P_{ed}=Ae^{\beta Ved}$) and arterial elastance (end-systolic pressure/stroke volume, Ea) an index of arterial resistance and compliance. Arterial load can be characterized by arterial elastance (Ea) which incorporates resistance, total vascular compliance (primarily determined by aortic compliance), characteristic impedance and systolic and diastolic time intervals. Ea is expressed in the pressure volume domain as end systolic pressure/stroke volume (Knowles et al., 2001. Pressure-independent enhancement of cardiac hypertrophy in natriuretic peptide receptor A-deficient mice. J Clin Invest 107:975–984; Barbee et al., 1994. Hemodynamics in transgenic mice with overexpression of atrial natriuretic factor. Circ Res 74:747–751; and Yamamoto et al., 2000. Left ventricular diastolic dysfunction in patients with hypertension and preserved systolic function. Mayo Clin Proc 75:148–155). Thus, use of the conductance catheter can determine whether the hypertension in this models is due to increased cardiac output or increased vascular stiffness (Ea).

Murine echocardiography: Avertin anesthetized mice can undergo 2-dimensional targeted M-mode echocardiography (GE System 5, Horten, Norway) with a 10 MHz probe. Digital images are analyzed on the system work station. LV end-diastolic (LVd) and end-systolic (LVs) dimensions and septal (IVSd) and posterior (PWd) diastolic wall thickness are measured. Fractional shortening, average wall-thickness and LV mass are calculated as previously described (Hart et al., 2001. Effects of avertin versus xylazine-ketamine anesthesia on cardiac function in normal mice. Am J Physiol Heart Circ Physiol 281:H1938–1945). The animal is placed prone on an elevated open center platform containing a 1.25 cm Cincinnati Standoff Acoustic Gel Pad allowing access of the ultrasound transducer to the left chest wall from below and through the standoff. The standoff provides an increase in the distance between the probe and the chest wall with favorable acoustic properties enhancing image quality. Imaging of the heart is performed at an average depth of 2.0–2.5 cm. Ultrasonic gel is placed between the mouse and the standoff to enhance contact and image quality. Simultaneous electrocardiography is obtained. A heat lamp is used to maintain body temperature during imaging.

LV two-dimensional (2D) and M-mode images are obtained with a 10-MHz ultrasonic transducer (General Electric Systems Five). LV M-mode tracings are obtained under 2D guidance using the 2D parastemal long-axis and 2D short-axis views at the level of the papillary muscles just distal to the mitral valve leaflet tips. End-diastoleis defined as the maximal LV diastolic diameter at the peak of the R wave on the EKG, and end-systole is defined as the peak of the LV posterior wall motion. M-mode measurements are made in accordance with the American Society of Echocardiography leading-edge convention using the steepest continuous endocardial echoes. Measurements include LV end-diastolic (LVDd) and end-systolic dimensions (LVDs), septal wall end-diastolic ($Sth_d$) and end-systolic thicknesses ($Sth_s$), and posterior wall end-diastolic ($PWth_d$) and end-systolic thicknesses ($PWth_s$). Diastolic wall thicknesses are averaged for average wall thickness. Fractional shortening (FS), ejection fraction (EF) and LV mass are calculated using standard formulae:

$$FS(\%) = [(LVDd - LVSd)/LVDd] * 100;$$

$$EF(\%) = [(LVDd^2 - LVSd^2)/LVDd^2] * 100;$$

$$LV \text{ Mass (g)} = 1.04 * [(LVDd + Sth_d + PWth_d)^3 - LVDd^3]$$
where 1.04 is the sp. gravity of the myocardium in g/ml Images are digitally acquired, stored, and analyzed off line using an image-analysis system (EchoPAC, GE Ultrasound). The GE system five has several advantages for murine echocardiography including: (1) high frame rates (up to 300 fps) which yield better resolution images at the heart rates present in mice, (2) digital acquisition and storage preventing image degradation associated with analog to digital conversion of images, and (3) digital storage of data allowing processing of acquired data such that image contrast, speed, etc can be adjusted on stored images. Further, M mode images can be acquired from stored 2D images and analyzed. This feature allows "anatomic" M-mode images such that the M-mode image can be acquired at a truly perpendicular angle instead of at the one angle present with real time M-mode imaging. In addition, digital storage with off-line analysis can allow the operator to concentrate on high quality image acquisition without consuming time making measurements. This limits the time needed to image the mouse and the amount of anesthesia required.

Echocardiographic observer variability. Agreement between observers is possible. Use of a single highly trained and experienced echocardiographic technician can further enhance reproducibility of data.

Atherosclerotic plaque analysis. The proximal portion of the thoracic aorta up to the aortic origin are isolated, are fixed with 10% Formalin, are cut open longitudinally. Atherosclerotic plaque areas are visible without staining. The images of the open luminal surface of the vessels are captured at a resolution of 512×512 by a red-green-blue three-chip charge-coupled device digital camera mounted on a dissecting microscope and recorded on an attached computer in 24-bit true image format. The analyses of the images are performed using C-Simple software (C. Imaging 1208, Compix, Mars, Pa.). The atherosclerotic plaque area is quantified and expressed as a percentage of the total luminal surface area of the thoracic aorta.

Nitric oxide synthase (NOS) assay. NOS activity is measured in aortic tissues. After flash freezing in liquid nitrogen, aortic tissues are stored $-80°$ C. The degree of subcellular localization of NOS depends largely on the isoform. eNOS (type 3) is contained largely in the insoluble pellet due to its membrane association through N-terminal myristoylation and palmitoylation. eNOS is prepared by extraction of membranes. To the aortas, 10 volumes of ice-cold homogenization buffer (50 mM Tris.Cl, pH 7.4, 1 mM EDTA, 0.1 mM PMSF) is added. The tissues are homogenized on ice using a polytron homogenizer. The homogenate is transferred to a centrifuge tube and is centrifuged for 15 minutes at 15,000×G at 4° C. The pellet is re-suspended in 3 volumes of extraction buffer (50 mM Tris.Cl, pH 7.4, 1 mM EDTA, 20 mM CHAPS. Immediately before use, 0.1 mM PMSF is added. The tube is gently rotated for 20 minutes at 4° C., and the mixture is centrifuged for 5 minutes at 13,000×G at 4° C. Most of the eNOS can be present in the supernatant. The two supernatants are combined for measurement of eNOS activity. Prior to measurement of eNOS, protein is quantitated. NOS activity is measured by quantifying the production of radioactive citrulline from arginine. Citrulline is separated from arginine by use of Dowex AG50WX-8 ion-exchange resin column chromatography. The reaction is performed in tubes containing 40 µl buffer [constituted from 50 µL of 10× reaction buffer (200 mM HEPES, pH 7.4, 10 mM ETDA, 12.5 mM $CaCl_2$), 50 µL 10 mM NADPH, 10 µL 50 µCi/mL [$^{14}$C] arginine, 290 µL water]. Calmodulin is added to 0.1 µM. To initiate the reaction, 10 µL of NOS-containing extract are added to give a final volume of 50 µL. To measure background signal, a control reaction is set up by adding 5 µL of 10 mM NAME and 5 µL of extract to 40 µL reaction mixture. Incubations are allowed to proceed for 30 minutes at 37° C. The reaction is terminated by adding 400 µL stop solution (20 mM HEPES, pH 5.5, 2 mM ETDA). The reactions are transferred to Dowex AG50WX-8 ion-exchange resin columns equilibrated in stop solution. The effluent is collected in a scintillation vial, and the column is washed with another 200 µL of stop solution. 10 mL of scintillation fluid are added to each vial and radioactivity is quantitated. NOS activity is calculated for each sample by subtracting the control value (NAME-treated) from that of the sample. Absolute NOS activity µmol/minute/µg protein= [sample (CPM)−NAME (CPM)]/counting efficiency (CPM/DPM)/$2.2×10^6$ (DPM/µCi)/specific activity of [$^{14}$C arginine (µCi/µmol)/incubation time (minutes)/input protein (µg).

Guanylate cyclase assay. [$\alpha$-$^{32}$P]GTP is used as substrate to monitor the yield of [$^{32}$P]cGMP. On ice, 12×75-mm glass reaction tubes for assays and controls to be performed in triplicate are set up. Three extra tubes each for maximum radioactivity (max) and background (blank) controls are set up as well. The following are added to all tubes: 50 µl 4× guanylate cyclase reaction mix (0.5 mg creatine phosphate, disodium salt, 2 µl 5 U/µl creatine phosphokinase; 5 µl 1 M Tris-acetate, pH 7.6; 1 µl 1 M magnesium acetate; 20 µl 20 mM cGMP; 1 µl $2×10^9$ cpm/ml [$^{32}$P]GTP; 2 µl 10 mg/ml BSA; 2 µl 10 mM IBMX; $H_2O$ to 50 µl); 20 µl 0.2 mM GTP; 80 µl 1 M Tris-acetate; 25 µl 50 mM magnesium acetate. The contents of the max tubes are transferred to scintillation vials. The sample and blank tubes are treated for 30 sec in a 30° C. water bath. 25 µl of the tissue homogenate (10 to 100 µg protein) is added to each sample tube, and 25 µl boiled tissue homogenate is added preparation to each control tube, to initiate the reaction. Tubes are incubated for 20 min at 30° C. The reaction is terminated with 250 µl of 200 mM zinc acetate/cGMP stop solution containing 10,000 cpm [8-$^3$H]GMP (5.8 Ci/mmol). 250 µl of 200 mM Na$_2$CO$_3$, are added, the mixture is vortexed mix on ice, and the mixture is centrifuged for 10 min at 500×G at room temperature. The supernant is discarded, and 1 ml of 1.0 N perchloric acid is added. 1 ml of the acidified samples and blanks are applied to alumina columns. The columns are washed with 10 ml H$_2$O, and the eluate is discarded. [$^3$H]- and [$^{32}$P]cGMP is eluted into scintillation vials with 3 ml of 200 mM ammonium formate. The amount of cGMP formed in each assay is calculated and is expressed as [$^{32}$P]cGMP formed in pmol/min/mg.

Adenylate cyclase assay (Enna et al., 2003. MEASUREMENT OF GUANYLATE CYCLASE ACTIVITY IN VITRO: John Wiley and Sons, Inc.): [α-$^{32}$P]ATP is included in the reaction mixture so that formation of radiolabeled cAMP can be monitored directly. After termination of the reaction by acid quench, the reaction products are separated by double-column chromatography. The following is added to the glass tubes: 50 µl 4× adenylate cyclase reaction mix (1 mg creatine phosphate, disodium salt, 2 µl 5 U/µl creatine phosphokinase, 5 µl 1 M Tris-acetate, pH 7.6, 1 µl 1 M magnesium acetate, 2 µl 100 mM EGTA, 20 µl 10 mM cAMP, 2 µl 100 mM DTT, 2 µl 10 mg/ml BSA, 2 µl 10 mM IBMX, 4 µg myokinase, H2O to 50 µl), 20 µl 5 mM ATP, 20 µl 10$^8$ cpm/ml [$^{32}$P]ATP (1×10$^7$ cpm/ml final in assay), 60 µl 1 M Tris-acetate. Sample and blank tubes are incubated for 30 sec in a 30° C. water bath. 50 µl of tissue homogenate (or boiled blank, 10–100 µg protein) is added to each sample tube to initiate the reaction. Sample and blank tubes are incubated for 20 min at 30° C., and the reaction is terminated by adding 800 µl cAMP stop solution. Dowex followed by alumina chromatography is carried out, and the eluate containing cAMP is quantitated by scintillation counting.

Cyclic AMP and cyclic GMP assay: Cyclic AMP and cyclic GMP are measured by immunoassay (Amersham Biosciences).

Cyclic GMP-dependent Protein Kinase Activity: This measurement is made using a kit from CycLex (Japan).

Measurement of cGMP phosphodiesterase and cAMP phosphodiesterase activities: Both cGMP phosphodiesterase and cAMP phosphodiesterase activities are measured using FlashPlate assays from Perkin Elmer (SMP001 and SMP002, PE Life Sciences, Boston). The assays involves adding a source of PDE and [$^{125}$I]cAMP or [$^{125}$I]cGMP to a FlashPalte, which contains an antibody to either cAMP or cGMP. PDE is used to catalyze the breakdown of cAMP or cGMP to their respective 5' nucleotides. The antibody does not bind to the catalyzed product. Alternatively, cGMP phosphodiesterase is measured in the cytoplasm of cells using a two-step radioisotope procedure as described elsewhere (Hosogai et al., 2003. Phosphodiesterase type 5 inhibition ameliorates nephrotoxicity induced by cyclosporin A in spontaneous hypertensive rats. Eur J Pharmacol 477:171–178; Thompson and Appleman, 1971. Multiple cyclic nucleotide phosphodiesterase activities from rat brain. Biochemistry 10:311–316).

Measurement of thiobarbituric acid reactive substances (Senthil et al., 2004 Evidence of oxidative stress in the circulation of ovarian cancer patients. Clin Chim Acta 339:27–32): Lipid peroxidation is estimated by the measurement of thiobarbituric acid reactive substances (TBARS) in plasma by a colorimetric method.

Measurement of plasma NO levels: Plasma NO levels are determined by measuring plasma NO$_2$/NO$_3$ levels using a nitrate/nitrite colorimetric assay kit (Cayman Chemical, Ann Arbor, Mich.).

Assays for prostaglandins: PGE metabolites, 6-keto-prostaglandin F1α, 2,3-dinor thromboxane B2 and isoprostanes are measured using specific kits from Cayman Chemicals.

Plasma renin activity, direct/active renin and angiotensin II assays: These are measured in plasma using kits and reagents for plasma renin activity (Diasorin Renctk), active or direct renin (Nichols Institute) and angiotensin II (SPI-bio).

Plasma endothelin: This is measured using a radioimmunoassay kit form Penninsula Laboratories.

Nitrites and Nitrates: These are measured using a kit for Cayman Chemical.

Western blotting for NO pathway proteins: Homogenates of aortic tissues are electrophoresed using SDS-polyacrylamide electrophoresis, electroblotting (Ausbel et al., 1998. Current Protocols in Molecular Biology. New York: John Wiley & Sons, Inc.; Towbin et al., 1979. Electrophoretic transfer of proteins from polyacrylamide gels to nitrocellulose sheets: procedure and some applications. Proc Natl Acad Sci USA 76:4350–4354; Sambrook and Russel, 2001. A Laboratory Manual. Cold Springs Harbor, New York: Cold Spring Haror Laboratory Press; and Laemmli, 1970. Cleavage of structural proteins during the assembly of the head of bacteriophage T4. Nature 227:680–685) and appropriate antibodies for endothelial nitric oxide synthase (Stressgen), soluble guanylyl cyclase (Cayman Chemicals), cGMP kinase (type 1α or 1β from Stressgen, or Chemicon), and type V cGMP-specific phosphodiesterase (Chemicon).

Example 4

Assessing Hypertension in Mice

The mechanism of hypertension in IEX-1 null mutant mice is assessed by examining responses to vasodilators in ex vivo systems such as aortic rings and mesenteric artery preparations. It is possible that the IEX-1 null mutant mice have an abnormality in the response to endogenously produced nitric oxide in large arterial vessels such as the aorta, and in resistance medium-small arteries such as the mesenteric artery. While it is possible that vasoconstrictor mechanisms or volume-dependent mechanisms are responsible for the genesis of hypertension, the data presented herein suggest that there are alterations in local vascular vasodilator systems in IEX-1 null mutant mice. Vasodilator systems that could be perturbed include the NO system. The results provided herein indicate that nitrite and nitrate production are increased in IEX-1$^{-/-}$ mice suggesting increased NO production with a concomitant resistance to NO action in the IEX-1$^{-/-}$ mice. Also, the data provided herein show no changes in urinary PGE2 or thromboxane B2, suggesting that there are no changes in prostaglandin action in vascular smooth muscle.

1. Ex Vivo Measurements of Endothelium-Dependent and -Independent Vasorelaxation of Aortic Rings in Organ Chambers:

Methods and materials similar to those described elsewhere can be used (Chan and Fiscus, 2001. Vasorelaxant response to isoprenaline, nitric oxide donor, calcitonin gene-related peptide and vasoactive intestinal peptide in aortic rings of adult C57BL/6J mice. *Eur J Pharmacol* 431: 229–236; Chan and Fiscus, 2003. Vasorelaxations induced by calcitonin gene-related peptide, vasoactive intestinal peptide, and acetylcholine in aortic rings of endothelial and inducible nitric oxide synthase-knockout mice. *J Cardiovasc Pharmacol* 41:434–443; Fiscus et al., 2001. CGRP release and synergistic interactions with nitric oxide: implications for pathogenesis of septic shock and the vascular problems of diabetes mellitus and aging. *ScientificWorldJournal* 1:2; Chan and Fiscus, 2003. Guanylyl cyclase inhibitors NS2028 and ODQ and protein kinase G (PKG) inhibitor KT5823 trigger apoptotic DNA fragmentation in immortalized uterine epithelial cells: anti-apoptotic effects of basal cGMP/PKG. *Mol Hum Reprod* 9:775–783; and d'Uscio et al., 2001. Mechanism of endothelial dysfunction in apolipoprotein E-deficient mice. *Arterioscler Thromb Vasc Biol* 21:1017–1022).

Briefly, IEX-1$^{+/-}$ mice are bred with one another to obtain homozygous knockout (IEX-1$^{-/-}$), homozygous normal (IEX-1$^{+/+}$), and heterozygous (IEX-1$^{-/+}$) littermate mice. Aortic rings from each group of mice are prepared with intact endothelium, or without endothelium (denuded rings) by established methods.

Aortic ring preparation. Age-matched male wild-type and IEX-1$^{-/-}$ knockout mice are euthanized with a mixture of ketamine/xylazine (100 mg/kg and 10 mg/kg, respectively, i.m.). From each, the thoracic aorta is quickly removed and is placed into a dissecting dish containing Krebs-Ringer Solution (K-R) maintained at 4° C. and continuously aerated with 5% $CO_2$ in oxygen. The K-R is comprised of (in mM) 118 NaCl, 4.7 KCl, 2.5 $CaCl_2$, 1.2 $KH_2PO_4$, 1.2 $MgSO_4$, 25 $NaHCO_3$ and 10 glucose; pH of final solution, 7.4. Each aorta is cleaned of perivascular tissue and is cut into rings 2 mm wide. Extreme care is taken to minimize stretching the vessels. In some experiments, the functional integrity of the endothelium is maintained, thus allowing only minimal touching of the vessel's luminal surfaces. For other experiments, the endothelium is deliberately removed by inserting a dissecting pin through the lumen and gently rolling the ring back and forth on filter paper submerged in K-R.

The rings are mounted for recording of isometric force, using a standard organ-bath apparatus (Radnoti Glass Technology, Monrovia, Calif.). For this, 2 horizontal stainless steel wires, 200 µm in diameter, are placed through the vessel lumen. The straight bottom wire, affixed to a rigid rod, is used to hold the ring in place, while the triangular-shaped second wire is attached to a force-transducer (FT-03D; Grass Instruments, Quincy, Mass.) placed above it for measurement of isometric force. The ring preparation is placed in an organ-bath filled with 8 ml K-R maintained at 37° C. and continuously aerated with the $O_2/CO_2$ mixture. A rack-and-pinion device attached to the transducer is used to allow manual adjustments of ring passive preload tension. Changes in force are recorded using data acquisition software (Labview 5.0; National Instruments, Austin, Tex.).

After mounting, each ring is equilibrated at minimal passive tension for 20 min. Thereafter, passive tension is incrementally increased, over a 30-min period, to the optimum point on the length-tension curve; 1 g, as determined in preliminary experiments. The ring is equilibrated under these conditions for 60 min after which maximal contraction is induced by exposure to $10^{-5}$ M of the thromboxane agonist U46619 (Cayman Chemical, Ann Arbor, Mich.). After contraction reaches a stable maximum plateau, an aliquot of the endothelium-dependent vasodilator acetylcholine (ACh; $10^{-6}$ M final concentration) is added to the bath to assess the functional integrity of the endothelium. Rings with ACh-induced relaxation of 50% or more are considered to have intact endothelium; those with relaxation of 10% or less are considered to be denuded of endothelium. The bath is rinsed with fresh K-R, and the ring is equilibrated, with several more rinses, for 45 min before further experimentation.

Specific Experiments with Aortic Rings:

A. NO-induced relaxation: In two separate experimental protocols, aortic rings from wild-type and an IEX-1$^{-/-}$ mice are paired in each experiment for a total of 10 experiments per protocol.

In the first experimental protocol, endothelium-dependent relaxation induced by ACh is assessed. Stable submaximal contraction of the rings is induced using $10^{-7}$ M U-46619. Thereafter, relaxation is assessed in response to ACh applied in incremental concentrations ranging from $10^{-9}$ M to $10^{-5}$ M. The ring preparation is rinsed for 30 min in fresh K-R containing the superoxide dismutase mimetic MnTBAP ($10^{-5}$ M; Calbiochem, San Diego, Calif.), and after this period the ACh relaxation curve is repeated to assess the potential involvement of superoxide anion in the relaxation response.

In a second experimental protocol, responsiveness to nitric oxide is assessed in paired endothelium-denuded rings. As described above, stable submaximal contraction is initially induced using $10^{-7}$ M U-46619. Thereafter, relaxation is assessed in response to the nitric oxide donor diethylamine/NO (Dea/NO; Calbiochem) applied in incremental concentrations ranging from $10^{-9}$ M to $10^{-5}$ M.

Western blot analysis of MA for endothelial, inducible and neuronal nitric oxide synthase, soluble guanylyl cyclase, cGMP kinase, type 5 phosphodiesterase (cGMP specific), myosin light chain kinase and non-phosphorylated and phosphorylated myosin light chain is performed after each experiment to determine how these variables change in response to various stimuli.

The following results are possible. There can be a blunted response to Ach. The response to a NO donor can be blunted as well if there is a defect in signaling via the cGMP pathway. This can be reflected in the reduction in cGMP kinase activity and amount, and a decrease in MLCK phosphorylation. If, however, the main defect is in the degradation of NO, then relaxation of the rings can be restored by the administration of Mn-TBAP (Mn(III) tetrakis-(4-benzoic acid) porphyrin.

2. Responses of Mesenteric Artery to Vasodilators:

Methods and materials similar to those described elsewhere can be used (Taylor et al. 2003. Altered expression of small-conductance Ca2+-activated K+ (SK3) channels modulates arterial tone and blood pressure. *Circ Res* 93:124–131; and Tsuneyoshi et al., 2003. Ca2+- and myosin phosphorylation-independent relaxation by halothane in K+-depolarized rat mesenteric arteries. *Anesthesiology* 99:656–665).

Isolated pressurized mesentery artery preparartion. Mesenteric arteries from male wild-type and IEX-1$^{-/-}$ mice are used to examine concurrent changes in smooth muscle intracellular $Ca^{2+}$ concentration ($[Ca^{2+}]_i$) and vessel diameter. Each mouse is euthanized as described above. From each, the mesentery is quickly removed en-bloc and is placed in a dissecting dish containing K-R maintained at 4° C. and continuously aerated with the $O_2/CO_2$ mixture. A 3 mm segment of second-order mesenteric artery, (about 100 µm in luminal diameter) is dissected and is placed in a small dish containing K-R. The ends of the segment are pinched shut temporarily. Additional K-R is gently introduced into the arterial lumen. In some experiments, the endothelium is deliberately removed by infusing an air bubble into the lumen for 2 min, followed by brief gentle perfusion with K-R (an alternative approach is to chemically remove the endothelium with saponin). These segments are loaded with fura 2-AM, a $Ca^{2+}$-sensitive fluorescent dye. For this, a small aliquot of 1 mM fura 2-AM, dissolved in DMSO, is mixed with an equal volume of a 25% (w/v) solution of pluronic acid in DMSO, then is diluted in 1 ml K-R to yield a final concentration of fura 2 AM of 5 μM. Each vessel is loaded in this solution for 60 min at room temperature, then is rinsed in fresh K-R.

The intact and endothelium denuded vessels are mounted between two glass cannulae in an arteriograph (Living Systems Instrumentation, Burlington, Vt.) positioned on an inverted microscope (Nikon TE300; Nikon Inc., Melville, N.Y.), and superfused continuously at 5 ml/min with oxygenated K-R at 37° C. The vessel is equilibrated under these conditions for 20 min. Thereafter, the vessel is gradually pressurized to 50 mm Hg via a servo-controlled pressure system (Living Systems). The luminal K-R is maintained in a no-flow situation. Vessel fura 2 fluorescence is measured using a photomultiplier system (IonOptix, Milton, Mass.) in which background-corrected ratios of the 510-nm emission from the arteries alternatively excited at 340 and 380 nm obtained at a sampling rate of 10 Hz. Arterial diameter is simultaneously measured by videomicroscopy (IonOptix).

Measurement of Smooth Muscle Contraction: Contraction and relaxation of smooth muscle is determined by continuous measurement of vessel diameter using a real-time image analysis system.

Measurement of Smooth Muscle $[Ca^{2+}]_i$: After removal of the endothelium, the smooth muscle is "loaded" with fura-2, using a stock solution of fura-2 acetoxymethyl ester (Molecular Probes) diluted to 10 μM in PSS containing bovine serum albumin, 0.2%. The fura-2 loading solution is placed in the bath for 2 h at room temperature. After loading, the tissue is washed with PSS, and the bath temperature is increased to 37° C. After subtraction of the background fluorescence, the ratio of the fura-2 fluorescence emission intensities at the 340- and 380-nm excitation wavelengths is calculated. $[Ca^{2+}]_i$ is calculated as described, using a dissociation constant for fura-2 of 224 nM (Grynkiewicz et al., 1985. A new generation of Ca2+ indicators with greatly improved fluorescence properties. *J Biol Chem* 260:3440–3450).

Specific experiments with mesenteric arteries: In two separate experimental protocols, pressurized (50 mm Hg) mesenteric arterial segments from wild-type and an IEX-$1^{-/-}$ mice are paired in each experiment for a total of 10 experiments per protocol. In the first experimental protocol, endothelium-dependent relaxation induced by ACh is assessed. Stable submaximal contraction of the arterial segments is induced using $10^{-7}$ M U-46619. Thereafter, relaxation is assessed in response to ACh applied in incremental concentrations ranging from $10^{-9}$ M to, $10^{-5}$ M. The arterial segments are rinsed for 30 min in fresh K-R containing $10^{-5}$ M MnTBAP, and ACh relaxation responses are repeated to assess the potential involvement of superoxide anion in the relaxation response.

In a second experimental protocol, relaxation and $[Ca^{2+}]_i$ responses to nitric oxide are assessed in endothelium-denuded arterial segments. As described above, stable submaximal contraction is initially induced using $10^{-7}$ M U-46619. Thereafter, relaxation and $[Ca^{2+}]_i$ responses to the nitric oxide donor Dea/NO applied in incremental concentrations ranging from $10^{-9}$ M to $10^{-5}$ M are assessed.

The following results are possible. There is a possibility that there will be a blunted response to Ach. The response to a NO donor can be blunted as well if there is a defect in signaling via the cGMP pathway. This can be reflected in the reduction in cGMP kinase activity and amount, and a decrease in MLCK phosphorylation. Changes in intracellular Ca can be blunted following Ach treatment. If, however, the main defect is in the degradation of NO, then relaxation of the rings can be restored by the administration of Mn-TBAP (Mn(III) tetrakis-(4-benzoic acid) porphyrin.

Example 5

Assessing Vascular Smooth Muscle Cells (VSMCs)

It is possible that IEX-1 alters the biological behavior of VSMCs by associating with specific nuclear proteins such as transcription factors and by associating with promoter elements of key genes. The following can be performed:

1. VSMCs can be cultured from IEX-$1^{-/-}$ and IEX-$1^{+/+}$ mice to determine whether there are differences in the rate of growth, apoptosis, and responses to growth factors in VSMCs from knockout or wild type mice.
2. To determine which genes or regulatory molecules are altered in IEX-1 knockout cells vs. normal cells, gene array analysis of mRNA obtained from these cells can be performed.
3. IEX-1 has motifs (e.g., the LXXL motif) that suggest that it binds with other proteins or transcription factors. Furthermore, it is apparent that IEX-1 alters cellular apoptosis and growth by altering the activity of various signaling molecules. In addition, using yeast two hybrid methods, it was shown that IEX-1 binds with CAML (calcium-modulating cyclophilin ligand), which can be involved in the control of apoptosis. To clarify the mechanism of action of IEX-1 in VSMCs, the VSMC proteins that bind IEX-1 can be identified using yeast two-hybrid systems.
4. Since there is good evidence that IEX-1 is a nuclear protein and that it influences the activities of various signaling molecules, it is likely that it associates with promoters of various genes. Chromatin immuno-precipitation cloning methods can be used to determine which nuclear proteins and gene promoters interact with IEX-1 protein.

1. Culture of VSMCs from IEX-$1^{-/-}$ and IEX-$1^{+/+}$ Mice to Determine Whether there are Differences in the Rate of Growth, Apoptosis and Response to Growth Factors in these Cells.

Methods and materials similar to those described elsewhere can be used (Ray et al., 2001. Isolation of vascular smooth muscle cells from a single murine aorta. Methods Cell Sci 23:185–188). These methods can allow for the isolation of relatively large numbers of cells within a period of a week in a predictable manner. Mice are euthanized using sodium pentobarbital. The thorax is opened to expose the heart and lungs. The aorta is dissected out from the origin at the left ventricle to the iliac bifurcation. The left ventricle is punctured, and the aorta is perfused with 3 mL of sterile PBS. The aorta is removed and is placed in a 100 mm Petri dish in 0.5 mL of Fungizone solution (10 μL of 0.25 mg/mL solution in 10 mL DMEM). The adventitia is removed from the aorta under a dissecting microscope. The aorta is cut into pieces of approximately 2 mm in size. The pieces are then placed in small tissue culture tubes containing 100 μL if enzyme solution (7.5 mg collagenase (type II, Worthington Biochemical Corporation) in 5.5 mL of DMEM). The aortas in enzyme solution are placed in a tissue culture incubator at 37° C., 5% $CO_2$ atmosphere for 6 hrs. The cells are re-suspended gently. 3 mL of DMEM containing 10% fetal bovine serum (FBS), 1% penicillin/streptomycin, and 1% glutamine is then added. The entire solution is then transferred to a 15 mL conical polypropylene tube and is centrifuged for five minutes at 300×G at room temperature. The medium is aspirated, and cells are then re-suspended in 5 mL of fresh medium. The cells are centrifuged and re-suspended in 700 µL of culture medium, and are transferred to a single well of a 48-well plate. The cells are allowed to grow for 5 d. Generally, 6,000 cells per well are obtained after 7–10 d of culture. To verify the phenotype, cells are stained, with antibodies directed against smooth muscle-specific proteins such as smooth muscle α-actin and calponin. Typical purity can be in the range of 99%.

Analysis of Cellular Growth: To assess cellular growth, cells are counted using a Coulter counter at intervals following plating at low density.

Analysis of Apoptosis

Methods and materials similar to those described elsewhere can be used (Ausbel et al., 1998. Current Protocols in Molecular Biology. New York: John Wiley & Sons, Inc.; and Colligan et al., 1994. Current Protocols in Immunology: John Wiley and Sons, Inc.). To assess apoptosis, the following assays are performed in sub-confluent and confluent VSMCs. UV light, camptothecin or serum deprivation is used to induce apoptosis in VSMCs. For UVB treatment, a FS20 UV lamp is used, with main emmittance in the UV-B range, peaking at 313 nm. The distance from the light source filter to the sample can be 10 cm, resulting in a radiation energy dose of 2.2 $J/m^2/s$ (133 $J/m^2/min$). Prior to irradiation, medium is removed from the cells. The dish is washed once with PBS at 37° C. to remove detached cells and components that could interfere with irradiation (e.g. phenol red). One ml or 10 ml PBS are added to T60 or T175 dishes respectively to avoid desiccation of the cell culture during irradiation. For UVA irradiation, F20/T12/BL/HO bulbs are used that emit at a peak range of 365 nm. A dose range of 10–50 $J/cm^2$ can be used. Alternatively, the polymerase I inhibitor, camptothecin (5 mM) in DMSO is added to cells in medium to induce apoptosis. Cells are incubated for various time periods. Serum deprivation is carried out by replacing growth medium with serum free medium.

Caspase 3 activity can be assessed with the Ac-DEVD-AMC synthetic tetrapeptide fluorogenic substrate (PharMingen). Cells are grown to 90% confluency, harvested and lysed in cold lysis buffer. Cell debris is separated from lysate by centrifugation. Caspase 3 enzymatic activity is determined in supernatants by incubation of 5 µg AC-DEVD-AMC substrate with 50 µl lysate for 1 h at 37° C. and subsequent determination of the cleavage product measured by fluorogenic activity in a Cytoflor plate reader (excitation wavelength: 380 nm: emission wavelength: 460 nm).

To delineate specific caspase activation and its modulation by IEX-1 null or expressing VSMCs, ApoAlert caspase Assay Plates (BD Biosciences) are used. These plates measure activation of four different caspases, caspase-1, -3, -8, and -9 using specific substrates and a fluorometric method. This system can allow screening of additional caspases-1, -8, and -9 and determine if specific caspase pathways are preferentially modulated by IEX-1. Results of caspase 3 assays are confirmed with the Cell Death Detection ELISA$^P$-$_{LUS}$ Assay (BM), performed according to the manufacturer's directions. Pure isolated DNA-nucleosome complex, included in the kit, can serve as a positive control.

TUNEL and caspase 3 immunohistochemistry (IHC) assays can be performed.

A Fas assay can be performed. For skin sections or cultured mouse VSMCs, anti-Fas (CD95) antibody (Dako) is used 1:10 v/v for 2 hr incubation, and a secondary antibody conjugated with horseradish peroxidase-labeled polymer (Envision+system, Dako) undiluted for 30 min, room temperature is then used to counterstain.

Analysis of responses to platelet derived growth factor in IEX-1 expressing and null mutant VSMCs: If differences in growth rates are seen between IEX-1 expressing and null mutant cells, the following can be performed to determine whether this is secondary to changes in responses to platelet derived growth factor. Briefly, IEX-1 expressing (wild-type) and null mutant VSMCs are cultured as described above. 48 h prior to testing, sub-confluent cells are serum deprived and grown in DMEM containing 1% ITS. Cells are treated with PDGF-BB added to yield final concentrations of 2, 4, 6 and 8 ng/ml. Cell numbers are assessed at 24, 48, and 72 h. Downstream signaling molecules are assessed using the PathScan™ PDGFR tyrosine kinase activity assay kit from Cell Signaling Technology that allows multiplex western detection of the following downstream molecules activated by PDGF: phospho-PDGFR, phospho-SHP2, phospho-Akt and phospho-p44/42.

The following results are possible. It is likely that in the absence of IEX-1, there can be changes in cell growth and apoptosis. If previous transfection results in VSMCs hold true in vessel walls in situ and in cultured cells from knockout and null mutant animals, there can be a diminished rate of apoptosis in the null mutant cells. The Fas and activated caspase-3 immunostaining procedures and TUNEL, caspase-3 and ApoAlert caspase assay plates can provide sufficiently sensitive methods to detect altered apoptosis in vessels and VSMCs that either IEX-1 expressing or null cells. In addition, IEX-1 null mutant cells can be hyper-responsive to PDGF.

2. Determination of Altered Signaling Pathways in VSMCs of IEX-1$^{-/-}$ Mice:

DNA micro-array analysis of RNA derived from VSMCs of IEX-1$^{-/-}$ mice is performed and the results are compared to those obtained from RNA of VSMCs from IEX-1$^{+/+}$ mice (Kumar et al., 1998. A novel immediate early response gene, IEX-1, is induced by ultraviolet radiation in human keratinocytes. Biochem Biophys Res Commun 253:336–341; Im et al., 2002. Divergent regulation of the growth-promoting gene IEX-1 by the p53 tumor suppressor and Sp1. J Biol Chem 277:14612–14621; and Im et al., 2002. Characterization of a novel hexameric repeat DNA sequence in the promoter of the immediate early gene, IEX-1, that mediates I alpha,25-dihydroxyvitamin D(3)-associated IEX-1 gene repression. Oncogene 21:3706–3714). Analysis of differentially expressed signaling genes and RNAs can allow an initial determination of which signaling pathways are altered in null mutant cells versus normal cells. Results from gene chip analyses can be confirmed by quantitative RT-PCR. The results of such experiments can be further confirmed by examining specific pathways with antibody reagents.

The following result is possible. Specific apoptotic signaling pathways can be altered by IEX-1.

3. Determination of the Identity of Proteins Bound by IEX-1 Using Yeast Two-Hybrid Systems:

A yeast Gal4, two-hybrid system (Clontech) is used to examine IEX-1 interactions with other proteins. The IEX-1 cDNA is cloned into the DNA BD domain plasmid pGBKT7, and a cDNA library derived from VSMCs is cloned into the activation domain vector pACT2. Interactions between the expressed IEX-1-DNABD fusion protein and the proteins expressed from pACT2 as protein-AD domain fusion proteins are detected by virtue of histidine and adenine auxotrophies and by virtue of generation of α-galactosidase activity. Insert DNAs in the pACT2 vector are sequenced by DNA sequencing methods, and the identity of the inserts is established (Ausbel et al., 1998. Current Protocols in Molecular Biology. New York: John Wiley & Sons, Inc.; Lutz et al., 2003. Calbindin D28K interacts with Ran-binding protein M: identification of interacting domains by NMR spectroscopy. Biochem Biophys Res Commun 303:1186–1192; Sanger et al., 1977. DNA sequencing with chain-terminating inhibitors. Proc Natl Acad Sci USA 74:5463–5467; and Sanger et al., 1992. DNA sequencing with chain-terminating inhibitors. 1977. Biotechnology 24:104–108). Interactions between IEX-1 and the novel interacting protein are assessed after in vitro trancription and translation of the IEX-1 protein and the novel protein as described earlier (Lutz et al., 2003. Calbindin D28K interacts with Ran-binding protein M: identification of interacting domains by NMR spectroscopy. Biochem Biophys Res Commun 303:1186–1192).

The following results are possible. The results of IEX-1 interaction with VSMC proteins can (a) indicate which signaling pathways are altered by IEX-1 as a result of direct IEX-1-protein interactions and (b) indicate whether IEX-1 associates with other transcription factors.

4. Determination of Gene Promoters and Nuclear Proteins with which IEX-1 Interacts Protein Using Chromatin Immuno-Precipitation Cloning Methods (Weinmann and Farnham, 2002. Identification of Unknown Target Genes of Human Transcription Factors Using Chromatin Immunoprecipitation. Methods 26:37–47):

VSMCs from IEX-1 expressing cells (wild type) are cultured. IEX-1 expression is verified by Western blotting. If it is absent or low, cells are transfected with an IEX-1 expression plasmid. $1 \times 10^7$ cells are used for each cross-linking. For cloning, multiple, identical cross-linking and immuno-precipitation reactions are performed and pooled at later steps. $1 \times 10^8$ cells can be used for 10 IP reactions. Formaldehyde is added directly to tissue culture medium to a concentration of 1%. Adherent cells are incubated on a shaking platform. The cross linking reaction is stopped by adding glycine to a final concentration of 0.125 M for 5 min. The medium is poured off, and the plates are washed twice with cold 1× PBS. The cells are lifted with trypsin treatment and scraping. Trypsin is inactivated with a small amount of serum containing medium. Scraped adherent cells are centrifuged at 1500 rpm and are washed once with 1× PBS plus PMSF. The pellet is resuspended in lysis buffer plus the protease inhibitors (PMSF/aprotinin/leupeptin). Cells are homogenized on ice with a Dounce homogenizer several times to aid in release of nuclei. Cells are centrifuged at 5000 rpm for 5 min at 4° C. to pellet the nuclei. The supernatant is discarded, and the nuclear pellet is resuspended in 1 ml nuclei lysis buffer plus protease inhibitors and incubated on ice for 10 min. Sonication of chromatin to an average length of approximately 1–2 kb is performed. After sonication, samples are centrifuged at 14,000 rpm for 10 min at 4° C. The supernatant is transferred to a new tube. Chromatin is pre-cleared by adding 50 μl of pre-blocked Staph A cells (for $10^8$ cross linked cells) and incubating on a rotating platform at 4° C. for 15 min. The mixture is then centrifuged at 14,000 rpm for 4 min, and the supernatant is transferred to a new tube and divided equally among 10 IP samples. 9 samples are precipitated with a 1:200 dilution affinity purified IEX-1 antibody (overnight at 4° C.), and 1 sample is used as a no antibody or pre-immune serum control. 10 μl of blocked Staph A cells are added to each sample and incubated on a rotating platform at 4° C. for 15 min. Samples are centrifuged at 14,000 rpm for 4 min. The supernatant from the "no antibody" sample is saved as "total input chromatin." For other samples, the supernatant is discarded, and the pellets are washed twice with 1.2 ml of 1× dialysis buffer and four times with 1.2 ml of IP wash buffer. After the last wash, samples are centrifuged at 14,000 rpm for 4 min, and the supernatant is removed. Antibody/protein/DNA complexes are eluted by adding 30 μl of IP elution buffer with vortexing for 30 min. Samples are centrifuged at 14,000 rpm for 4 min and transferred to new tubes and centrifuged again. 270 μl of dilution buffer (plus protease inhibitors) for each 30 μl of eluted samples are added. The samples are combined into approximately 600 μl per tube. A second immuno-precipitation with the same antibody to be used in first precipitation is carried out at 4° C. overnight. Antibody is removed using Staph A cells, and extensive washing is carried out. The pellets containing antibody/protein/DNA complexes are treated with 150 μl elution buffer, vortexed vigorously for 30 minutes, and centrifuged at 14,000 rpm for 5 minutes. The pellet are re-extracted, and the two supernatants are combined. The samples are treated with 1 μl of 10 mg/ml RNase A, and 12 μl of 5M NaCl are added to a final concentration of 0.3M. The samples are incubated for 5 h at 67° C. to reverse cross-links. 2.5 volumes of ethanol are added, and the samples are left at −20° C. overnight. For protein identification experiments, the samples are centrifuged at 14,000×G for 15 minutes at 4° C., and the supernatant are removed. The pellet is re-suspended in 100 μl TE, and DNAase is added to digest DNA. Proteins in the supernatant are separated by SDS-PAGE, are stained with Coomassie or silver stain, and are sequenced using Edman degradation methods and mass spectrometry after cryptic digestion.

For cloning experiments, samples are centrifuged at 14,000 rpm for 15–20 min at 4° C. The supernatant is discarded, and residual ethanol is removed by another centrifuge step. The pellets are allowed to air-dry and are dissolved in 100 μl of TE. 25 μl of 5× PK buffer and 1.5 μl of proteinase K (25 mg/ml) are added to each sample. The samples are incubated at 45° C. for 2 h. 175 μl of TE are added to each sample. Extraction once with 300 μl of phenol/chloroform/isoamyl alcohol and once with 300 μl chloroform/isoamyl alcohol are carried out. 30 μl of 5 M NaCl, 5 μg of glycogen, and 750 μl of ethanol are added to each sample, and the DNA is allowed to precipitate at −20° C. overnight.

Following centrifugation, the samples are resuspended in 30 μl water and combined. The total sample is re-suspended in 30 μl water. To create blunt-ended DNA fragments for cloning purposes, 60 μl of the experimental sample, 20 μl of 1 mM dNTPs, 20 μl of 10× T4 DNA polymerase buffer, 2 μl BSA, 10 mg/ml, 92 μl of water, and 6 μl of T4 DNA polymerase are added to the DNA. Incubation at 37° C. for 30 min is carried out. Following completion of the reaction, and phenol: chloroform extraction of the sample, DNA is recovered. The DNA pellet is resuspended pellet in 10 μl of water and is ligated into a vector previously digested with an enzyme that creates blunt ends. pUC19 vector digested with HincII is an example of an appropriate vector. Standard transformation reactions using the entire ligation mixture and competent bacterial cells (TOP 10 competent cells (Invitrogen)) is carried out. Cells are plated on media containing the appropriate antibiotic and are incubated overnight at 37° C. The next day, colonies are picked, and plasmid isolation is carried out after growth of colonies in liquid medium. Digestion of the chimeric plasmids with the appropriate restriction enzymes to release the cloned DNA insert is performed, and inserts are visualized by agarose gel electrophoresis. Cloned fragments of 500 bp or greater are likely to contain authentic promoter or other binding regions instead of nonspecific DNA such as that found in repeat regions. DNA sequencing of the cloned inserts using vector-specific primers is carried out. Clone-specific primers are designed to conduct independent chromatin immuno-precipitation experiments to confirm that the cloned fragment is specific to the antibody treatment and not due to the non-specific precipitation of the fragment.

The following results are possible. Proteins with which IEX-1 interacts within the nucleus can be identified. In addition, gene promoters that interact with IEX-1 in the event that it functions as a transcription factor can be identified.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claim is:

1. A transgenic mouse whose somatic and germ cells comprise a nucleic acid construct that disrupts the endogenous IEX-1 sequence, the disruption resulting in said transgenic mouse having a level of blood pressure that is higher than the level observed in a control mouse lacking said disruption, wherein said mouse is homozygous for said disruption and lacks expression of IEX-1 polypeptide.

2. The transgenic mouse of claim 1, wherein said transgenic mouse has a level of blood pressure that is 5 mm of Hg higher than the level observed in a control mouse lacking said disruption.

3. The transgenic mouse of claim 1, wherein said transgenic mouse has a level of blood pressure that is 10 mm of Hg higher than the level observed in a control mouse lacking said disruption.

4. The transgenic mouse of claim 1, wherein said transgenic mouse has a level of blood pressure that is 20 mm of Hg higher than the level observed in a control mouse lacking said disruption.

5. The transgenic mouse of claim 1, wherein said transgenic mouse has a level of blood pressure that is 30 mm of Hg higher than the level observed in a control mouse lacking said disruption.

6. A transgenic mouse comprising somatic and germ cells that are heterozygous for a nucleic acid construct that disrupts the endogenous IEX-1 sequence.

* * * * *